United States Patent [19]

Thompson et al.

[11] Patent Number: 6,159,460
[45] Date of Patent: Dec. 12, 2000

[54] METHOD FOR TREATING INTERLEUKIN-1 MEDIATED DISEASES

[75] Inventors: Robert C. Thompson; David F. Carmichael, both of Boulder, Colo.

[73] Assignee: Amgen Inc., Thousand Oaks, Calif.

[21] Appl. No.: 08/292,539

[22] Filed: Aug. 18, 1994

Related U.S. Application Data

[63] Continuation-in-part of application No. 08/002,074, Jan. 8, 1993, abandoned, and a continuation-in-part of application No. 08/171,873, Dec. 22, 1993, abandoned, and a continuation-in-part of application No. 08/171,876, Dec. 22, 1993, abandoned, and a continuation-in-part of application No. 08/171,867, Dec. 22, 1993, abandoned, said application No. 08/002,074, is a continuation-in-part of application No. 07/849,635, Mar. 5, 1992, abandoned, which is a continuation of application No. 08/502,745, Apr. 2, 1990, abandoned, which is a continuation-in-part of application No. 07/463,888, Jan. 11, 1990, abandoned, said application No. 08/171,873, is a continuation of application No. 08/047,765, Apr. 15, 1993, abandoned, which is a continuation of application No. 07/895,145, Jun. 5, 1992, abandoned, which is a continuation of application No. 07/524,210, May 16, 1990, abandoned, which is a continuation-in-part of application No. 07/502,745, Apr. 2, 1990, abandoned, said application No. 08/171,876, is a continuation of application No. 08/047,762, Apr. 15, 1993, abandoned, which is a continuation of application No. 07/895,153, Jun. 5, 1992, abandoned, which is a continuation of application No. 07/530,553, May 29, 1990, abandoned, which is a continuation-in-part of application No. 07/524,210, May 16, 1990, abandoned, said application No. 08/171,867, is a continuation of application No. 08/097,308, Jul. 26, 1993, abandoned, which is a continuation of application No. 07/936,874, Aug. 27, 1992, abandoned, which is a continuation of application No. 07/678,732, Apr. 1, 1991, abandoned, which is a continuation-in-part of application No. 07/530,553, May 29, 1990, abandoned.

[51] Int. Cl.[7] .................................................. A61K 38/19
[52] U.S. Cl. ................................. 424/85.1; 514/2; 514/8; 514/12; 514/885
[58] Field of Search .................... 514/8, 12, 21, 514/885; 530/350; 424/85.1

[56] References Cited

U.S. PATENT DOCUMENTS

| | | | |
|---|---|---|---|
| 4,935,343 | 6/1990 | Allison et al. | 435/7 |
| 4,956,381 | 9/1990 | Bollinger et al. | 514/443 |
| 4,968,607 | 11/1990 | Dower et al. | 435/69.1 |
| 5,041,554 | 8/1991 | Parker et al. | 548/532 |
| 5,075,222 | 12/1991 | Hannum et al. | 435/69.1 |
| 5,359,032 | 10/1994 | Dayer et al. | 530/350 |

FOREIGN PATENT DOCUMENTS

| | | |
|---|---|---|
| 0 398 817 A1 | 11/1990 | European Pat. Off. . |
| 0 343 684 B1 | 4/1993 | European Pat. Off. . |
| 0 541 920 A1 | 5/1993 | European Pat. Off. . |
| 27 06772 | 12/1994 | France . |
| 2-223597 | 9/1990 | Japan . |
| WO 89/01946 | 3/1989 | WIPO . |
| WO 89/11540 | 11/1989 | WIPO . |
| WO 91/00742 | 1/1991 | WIPO . |
| WO 91/08285 | 6/1991 | WIPO . |
| WO 91/17184 | 11/1991 | WIPO . |
| WO 91/17249 | 11/1991 | WIPO . |
| WO 92/12724 | 8/1992 | WIPO . |
| WO 92/16221 | 10/1992 | WIPO . |
| WO 93/02692 | 2/1993 | WIPO . |
| WO 93/08304 | 4/1993 | WIPO . |
| WO 93/08820 | 5/1993 | WIPO . |
| WO 93/18783 | 9/1993 | WIPO . |
| WO 93/21946 | 11/1993 | WIPO . |
| WO 93/24134 | 12/1993 | WIPO . |
| WO 94/06457 | 3/1994 | WIPO . |
| WO 94/20517 | 9/1994 | WIPO . |
| WO 94/21235 | 9/1994 | WIPO . |
| WO 94/21275 | 9/1994 | WIPO . |
| WO 95/10298 | 4/1995 | WIPO . |
| WO 95/16353 | 6/1995 | WIPO . |
| WO 95/16706 | 6/1995 | WIPO . |
| WO 96/09323 | 3/1996 | WIPO . |

OTHER PUBLICATIONS

Bowie et al. Science 1990, vol. 247, pp. 1306–1310.
Tan et al. Australian & New Zealand Rhematism Associations. p. 113 (1986).
Biotechnology Bulletin, Jun. 31, 1994, vol. 13, No. 6, p. 2.
Bulletin International d'Informations (Droit et Pharmacie) Sep. 21, 1994, Aug. 9, p. 89.
Seckinger et al. (1987) J. of Immunol. vol. 139. pp. 1546–1549.
Seckinger et al. (1987) Ann. Inst. Pasteur Immunol. vol. 138. pp. 486–488.
Okusawa et al. (1988) J. Clin. Invest. vol. 81. pp. 1162–1172.
Sullivan et al. (1988) Infection & Immunity vol. 56 pp. 1722–1729.
Cominelli et al. (1989) Biotherapy vol. 1, pp. 369–375.
Dinarello et al. (1988) Digestive Diseases & Sciences vol. 33, pp. 255–355.
Billingham (1985) Br. J. of Rhematology vol. 24, pp. 25–28.
Pujol et al. (1987) Life Sciences vol. 41 pp. 1187–1198.
Relton & Rothwell , *Brain Res. Bull.* 29:243–246 (1992).
Rothwell & Relton, *Neurosci. Biobehav. Rev.* 17:217–227 (1993).
Conti et al, *Int. J. Immunopharmae* 14(6):987–993 (1992).
Seckinger et al, *J. Immunol.* 139:1546–1549 (1987).
Pujol & Loyau, *Life Sciences* 41:1187–1198 (1987).
Eisenberg et al, *Nature* 343:341–346 (1990).
Tan et al, *Australian & New Zealand Rheumatism Assoc. 1987* 17(1):113 (Abstract).
Seckinger & Dayer, *18th Forum in Immunol.* 486–488 (1987).

(List continued on next page.)

*Primary Examiner*—Prema Mertz
*Attorney, Agent, or Firm*—Finnegan, Henderson, Farabow, Garrett & Dunner, L.L.P.

[57] ABSTRACT

The present invention provides methods for treating interleukin-1 mediated diseases including arthritis, inflammatory bowel disease, sepsis and septic shock, ischemia injury, reperfusion injury, multiple sclerosis and cerebral infarctions such as cerebral palsy. The methods are accomplished by administering to a patient in need thereof a therapeutically effective amount of an interleukin-1 inhibitor.

19 Claims, 4 Drawing Sheets

OTHER PUBLICATIONS

Billingham, *Br. J. Rheumatology* 24 (Suppl. 1):25–28 (1985).
Stimpson et al. *J. Immunol.* 140:2964–2969 (1988).
Hannum et al, *Nature* 343:336–340 (1990).
Arend et al, *J. Immunol.* 143(6): 1851–1858 (1989).
Cominelli et al, *Biotherapy* 1(4):369–375 (1989).
Cominelli et al, *Gastroenterology* 97(6): 1400–1405 (1989).
Dinarello, *Digestive Diseases & Sciences* 33(Suppl 3): 255–355 (1988).
Okusawa et al, *J. Clin. Invest.* 81(4): 1162–1172 (1988).
Sullivan et al, *Infect. Immunol.* 56(7): 1722–1729 (1988).
Dinarello, *Blood* 77(8): 1627–1652 (1991).
Cominelli et al, *J. Clin. Invest.* 86:972–980 (1990).
Ohlsson et al. *Nature* 348:550–552 (1990).
Ulich et al, *Am J. Pathology* 138(3):521–524 (1991).
Thomas et al, *Agents & Action* 34:187–190 (1991).
Seckinger et al, *J. Immunol.* 145:4181–4184 (1990).
Wakabayashi et al, *FASEB J.* 5(3):338–343 (1991).
Lotz et al, *Arthritis Rheum*, 29:S38 #162 (Abstract).
Poli et al, *Proc. Natl. Acad. Sci. USA* 91:108–112(1994).
Piguet et al, *Cytokine* 5(1): 57–61 (1993).
Wooley et al, *Arthritis & Rheumatism* 36(9): 1305–1314 (1993).
Rolfe et al, *Am. Rev. Respir. Dis.* 148:1378–1384 (1993).
Moldawer, *Blood Purif.* 11:128–133 (1993).
Pillay et al, *Pflugers Arch.* 424:549–551 (1993).
Ferrara, Keystone Symposium on Cellular Immunity & the Immuno–therapy of Cancer, Mar. 17–24, 1993, p. 96 (Abstract No. NZ 019).

Catalano, Keystone Symposium on Cytokines and Cytokine Receptors, Jan. 31–Feb. 7, 1993, p. 55 (Abstract No. E 016).

Cannon et al., "Circulating Interleukin–1 and Tumor Necrosis Factor in Septic Shock and Experimental Endotoxin Fever", *Journal of Infectious Diseases* 161:79–84 (1990).

Eichacker et al., "The Effects of Human Recombinant Interleukin–1 (IL–1) On Canine Alveolar Neutrophil (N) Number And Lung Function", *Critical Care Medicine*, Apr., 1989 p. S58.

Girardin et al, "Tumor Necrosis Factor and Interlukin–1 In The Serum of Children With Severe Infectious Purpura", *New England Journal of Medicine* 319(7):397–400 (1988).

Hilton et al., "A Report on the International Conference on Inflammation Held in Rome, Oct. 6–11, 1991", *DN & P*5(1):59–62 (1992).

Rosenstreich et al., "A Human Urine–Derived Interleukin1 Inhibitor: Homology with Deoxyribonuclease 1", *J. Exp. Med.* 168:1767–1779 (1988).

Takahashi K., "Basal and Clinical Investifation of Urine IL–1 Inhibitor", *Medical Journal of Hiroshima University*35(4):813–842 (1987).

Ziegler et al., "Treatment of Gram–Negative Bacteremia and Shock With Human Antiserum to a Mutant *Escherichia coli*", *New England Journal of Medicine* 307:1225–1230 (1982).

METHOD FOR TREATING INTERLEUKIN-1 MEDIATED DISEASES

CROSS REFERENCE TO RELATED APPLICATIONS

This application is a continuation-in-part of abandoned U.S. patent application Ser. No. 08/002,074, filed Jan. 8, 1993, abandoned U.S. patent application Ser. No. 08/171, 873, filed Dec. 22, 1993, abandoned U.S. patent application Ser. No. 08/171,876, filed Dec. 22, 1993, and abandoned U.S. patent application Ser. No. 08/171,867, filed Dec. 22, 1993, now abandoned all of which are incorporated herein by reference in their entirety.

U.S. patent application Ser. No. 08/002,074 is a continuation of abandoned U.S. patent application Ser. No. 07/849, 635, filed Mar. 5, 1992, which is a continuation of abandoned U.S. patent application Ser. No. 07/502,745, filed Apr. 2, 1990, which is a continuation-in-part of abandoned U.S. patent application Ser. No. 07/463,888, filed Jan. 11, 1990, which is a continuation of abandoned U.S. patent application Ser. No. 07/248,521, filed Sep. 23, 1988, which is a continuation-in-part of abandoned U.S. patent application Ser. No. 07/238,713, file Aug. 31, 1988, which is a continuation-in-part of abandoned U.S. patent application Ser. No. 07/199,915, filed May 27, 1988.

U.S. patent application Ser. No. 08/171,873 is a continuation of abandoned U.S. patent application Ser. No. 08/047, 765, filed Apr. 15, 1993, which is a continuation of abandoned U.S. patent application Ser. No. 07/895,145, filed Jun. 5, 1992, which is a continuation of abandoned U.S. patent application Ser. No. 07/524,210, filed May 16, 1990, which is a continuation-in-part of abandoned U.S. patent application Ser. No. 07/502,745, filed Apr. 2, 1990, which is a continuation-in-part of abandoned U.S. patent application Ser. No. 07/463,888, filed Jan. 11, 1990, which is a continuation of abandoned U.S. patent application Ser. No. 07/248,521, filed Sep. 23, 1988, which is a continuation-in-part of abandoned U.S. patent application Ser. No. 07/238, 713, filed Aug. 31, 1988, which is a continuation-in-part of abandoned U.S. patent application Ser. No. 07/199,915, filed May 27, 1988.

U.S. patent application Ser. No. 08/171,876 is a continuation of abandoned U.S. patent application Ser. No. 08/047, 762, filed Apr. 15, 1993, which is a continuation of abandoned U.S. patent application Ser. No. 07/895,153, filed Jun. 5, 1992, which is a continuation of abandoned U.S. patent application Ser. No. 07/530,553, filed May 29, 1990, which is a continuation-in-part of abandoned U.S. patent application Ser. No. 07/524,210, filed May 16, 1990, which is a continuation-in-part of abandoned U.S. patent application Ser. No. 07/502,745, filed Apr. 2, 1990, which is a continuation-in-part of abandoned U.S. patent application Ser. No. 07/463,888, filed Jan. 11, 1990, which is a continuation of abandoned U.S. patent application Ser. No. 07/248,521, filed Sep. 23, 1988, which is a continuation-in-part of abandoned U.S. patent application Ser. No. 07/238, 713, filed Aug. 31, 1988, which is a continuation-in-part of abandoned U.S. patent application Ser. No. 07/199,915, filed May 27, 1988.

U.S. patent application Ser. No. 08/171,867 is a continuation of abandoned U.S. patent application Ser. No. 08/097, 308, filed Jul. 26, 1993, which is a continuation of abandoned U.S. patent application Ser. No. 07/936,874, filed Aug. 27, 1992, which is a continuation of abandoned U.S. patent application Ser. No. 07/678,732, filed Apr. 1, 1991, which is a continuation-in-part of abandoned U.S. patent application Ser. No. 07/530,553, filed May 29, 1990, which is a continuation-in-part of abandoned U.S. patent application Ser. No. 07/524,210, filed May 16, 1990, which is a continuation-in-part of abandoned U.S. patent application Ser. No. 07/502,745, filed Apr. 2, 1990, which is a continuation-in-part of abandoned U.S. patent application Ser. No. 07/463,888, filed Jan. 11, 1990, which is a continuation of abandoned U.S. patent application Ser. No. 07/248,521, filed Sep. 23, 1988, which is a continuation-in-part of abandoned U.S. patent application Ser. No. 07/238, 713, filed Aug. 31, 1988, which is a continuation-in-part of abandoned U.S. patent application Ser. No. 07/199,915, filed May 27, 1988.

BACKGROUND OF THE INVENTION

The present invention describes methods for preventing or treating a variety of diseases and deleterious medical conditions associated with interleukin-1 (IL-1).

Cytokines are extracellular proteins that modify the behavior of cells, particularly those cells that are in the immediate area of cytokine synthesis and release. One of the most potent inflammatory cytokines thought to be a key mediatory in many diseases and medical conditions is IL-1. Interleukin-1 is manufactured, although not exclusively, by cells of the macrophage/monocyte lineage and is produced in two known forms, IL-1 alpha (IL-1$\alpha$) and IL-1 beta (IL-1$\beta$).

A disease or medical condition is considered an "interleukin-1 mediated disease" if the spontaneous or experimental disease or medical condition is associated with elevated levels of IL-1 in bodily fluids or tissue, or if cells or tissues taken from the body produce elevated levels of IL-1 in culture. In many cases, such IL-1 mediated diseases are also recognized by the following additional two conditions: (1) pathological findings associated with the disease or medical condition can be mimicked experimentally in animals by the administration of IL-1; and (2) the pathology induced in experimental animal models of the disease or medical condition can be inhibited or abolished by treatment with agents that inhibit the action of IL-1. In most IL-1 mediated diseases, at least two of these three conditions are met. Diseases or medical conditions that are IL-1 mediated include, for example, arthritis, inflammatory bowel disease, sepsis and septic shock, reperfusion injury, osteoporosis, asthma, insulin diabetes, myelogenous and other leukemias, psoriasis, cachexia/anorexia, multiple sclerosis, and ischemic injury, including cerebral infarctions such as cerebral palsy.

Arthritis is a chronic joint disease that afflicts and disables, to varying degrees, millions of people worldwide. The disease is typically characterized at the microscopic level by the inflammation of synovial tissue and by a progressive degradation of the molecular components constituting the joint cartilage and bone. Continued inflammation and erosion of the joint frequently lead to considerable pain, swelling, and loss of function. While the etiology of arthritis is poorly understood, considerable information has recently been gained regarding the molecular aspects of inflammation. This research has led to the identification of certain cytokines, which are believed to figure prominently in the mediation of inflammation. The involvement of interleukin-1 in arthritis has been implicated by two distinct lines of evidence. First, increased levels of interleukin-1 and of the mRNA encoding it have been found in the synovial tissue and fluid of arthritic joints. See G. Buchan et al., "Third Annual General Meeting of the British Society for Rheumatology," London, England, Nov. 19–21, 1988 *J. Rheumatol.* 25 (Supplement 2); Fontana et al., *Rheumatology Int.,* 2:49–53 (1982); Duff et al., *Monokines and Other Non-Lymphocytic Cytokines,* M. Powanda et al., editors, pp. 387–392 (Alan R. Liss, Inc. 1988).

Second, the administration of interleukin-1 to healthy joint tissue has been shown on numerous occasions to result in the erosion of cartilage and bone. In one experiment, intraarticular injections of IL-1 into rabbits were shown to cause cartilage destruction in vivo as described by Pettipher et al., *Proc. Nat'l Acad. Sci. U.S.A.,* 83:8749–8753 (1986). In other studies, IL-1 was shown to cause the degradation of both cartilage and bone in tissue explants. Relevant references include J. Saklatavala et al., *Development of Diseases of Cartilage and Bone Matrix,* pp. 291–298 (Alan R. Liss, Inc.) and Stashenko et al., *The American Association of Immunologists,* 183:1464–1468 (1987). One generally accepted theory used to explain the causal link between IL-1 and inflammation is that IL-1 stimulates various cell types, such as fibroblasts and chondrocytes, to produce and secrete proinflammatory or degradative compounds, such as prostaglandin E2 and collagenase.

Inflammatory bowel disease ("IBD") is a term used to describe both acute and chronic inflammatory conditions of the intestinal tract tissue and encompasses two generally distinct maladies known as ulcerative colitis and Crohn's disease. Ulcerative colitis is a mucosal ulceration of the colon. Crohn's disease, which is also referred to as ileitis, ileocolitis and colitis, is a transmural inflammation that can be found throughout the general intestinal tract.

IBD is characterized by various histological features including transmural acute and chronic granulomatous inflammation with ulceration, crypt abbesses and marked fibrosis. Not all of these indications, however, will be found in all IBD cases. Spontaneous reactivation, extraintestinal inflammation and anemia are often associated with IBD. Large joint arthritis is commonly found in patients suffering from Crohn's disease.

In the molecular processes of the inflammation associated with arthritis, research has found that various cytokines appear to mediate aspects of IBD. In particular, IL-1 has been implicated as a mediating material in IBD. Again, two distinct lines of evidence lead to this conclusion. Increased levels of IL-1 have been found in affected areas of intestines from patients with IBD. Tissues from patients with active ulcerative colitis showed IL-1 levels about 15 times the level found in control samples. Tissues with active Crohn's disease showed IL-1 levels about 6 times that of control, and tissues with inactive Crohn's disease were about three times that of the control tissue samples. See, Sartor et al., *Gastroenterology,* 94:A399; see also Satsangi et al., *Clin. Exp. Immunol.,* 67:594–605 (1987); Rachmilewitz et al., *Gastroenterology,* 67:594–605 (1989)(the bioassay used to determine IL-1 concentration levels is known to also unselectively detect IL-2, IL-4, IL-6 and IL-7).

The role of IL-1 in IBD has also been implicated by studies that have shown that the perfusion of rabbit colons with IL-1 induces the production of prostaglandin and thromboxane. Comminelli et al., *Gastroenterology,* 97:1400–1405 (1989). This finding is consistent with the hypothesis described above, i.e., IL-1 is linked with the inflammation of tissues due to its stimulatory effect of producing proinflammatory or degradative compounds. Thus, it is likely that systemic and local IL-1 production initiates or contributes to the inflammatory response in IBD, and plays an active role in the pathogenesis of the disease.

The systemic production of IL-1 may also be responsible, in part, for the extraintestinal inflammation associated with Crohn's disease.

Sepsis syndrome, referred to herein as "sepsis," is the systemic inflammatory response caused by microbial infection. For example, infections caused by the release of endotoxins by gram negative bacteria elicit the secretion of several cytokines including tumor necrosis factor alpha and IL-1. Sepsis, including septic shock and severe sepsis, is not caused directly by the invading microorganism. Rather, it is a result of an overwhelming cytokine response that induces pathologic changes in the host, including changes in thermoregulation, vascular permeability and resistance, cardiac function, bone marrow function, and the activity of key enzymes.

In the case of severe sepsis and septic shock, sepsis syndrome is characterized by periods of deteriorating organ function that may result in multiple organ dysfunction leading to death. Sepsis is the most common cause of death in intensive care units and statistics indicate that the incidence of the disease has substantially increased over the past decade. Septic shock for example, is characterized by various symptoms, including a drop in mean arterial blood pressure (MAP), a decrease in cardiac output, tachycardia, tachypnea, lacticacidemia and leukopenia. At present there are few treatment options for patients suffering from sepsis and septic shock, and the treatments available are generally supportive in nature rather than treatment for the pathologic condition.

That IL-1 may have a role in the mediation of sepsis and septic shock has been suggested by various studies. In one study of children suffering from gram-negative septicemia, elevated levels of IL-1 were found in 21% of the patients examined. In addition, it was shown that IL-1 serum levels were significantly higher in patients who died than in the survivors. Girardin et al., *New Engl. J. Med.,* 319:397–400 (1988); see also, Cannon et al., *Critical Care Medicine,* S58 (April 1989)(abstract).

It has also been shown that human IL-1 induces a shock-like state in rabbits. A single bolus injection of human IL-1β resulted in hypotension and several hemodynamic and hematological parameters characteristic of septic shock. For example, the mean arterial blood pressure of IL-1 injected rabbits decreased by a minimum of 19.1%. Okusawa et al., *J. Clin. Inves.,* 81:1162–1171 (1988).

Ischemic injury may occur to a tissue or organ whenever that tissue or organ is deprived of its normal blood flow. Further damage may occur when the flow of oxygenated blood is restored to that tissue. The extent and reversibility of the damage imparted depends partly on the severity of the original insult. It is possible, however, to mitigate the extent of tissue damage resulting from reperfusion by a variety of therapeutic interventions. Simpson et al., "Oxygen Radicals and Tissue Injury," *Brook Lodge Symposium - Upjohn* (B. Halliwell, ed. 1988).

Reperfusion injury is a well documented sequela to ischemic episodes in the heart, gut, kidney, liver and other organs. Simpson et al., supra; Herman et al., *FASEB J.,* 2:146–151 (1988); McDougal, *J. of Urology,* 140:1325–1330 (1988); Finn, *Kidney Int.,* 7:171–182 (1990); Schrier, *Klin. Wochenschr.,* 66:800–807 (1988); and Winchel, *Transportation,* 48:393–396 (1989). The exact pathogenesis of reperfusion injury may vary depending on the tissue affected. In the heart, for instance, reperfusion injury is accompanied by a dramatic influx of neutrophils, and these cells are thought to play a major role affecting the reperfusion damage (Lucchesi et al., *Ann. Rev. Pharmacol. Toxicol.*, 26:201–224 (1988)). Renal ischemia and reperfusion injury, on the other hand, appear to involve an increase in tubular cell membrane permeability, increased levels of intracellular calcium, altered mitochondrial respiratory function, and the generation of free radicals. In the kidney, the role of extravasating neutrophils in affecting the reperfusion injury is less certain. McDougal, *J. Urology*, 140:1325–1330 (1988); Finn, *Kidney Int.*, 37:171–182 (1990); Schrier, *Klin. Wochenschr.*, 66:800–807 (1988); and Winchel, *Transportation*, 48:393–396 (1989).

Despite the differences in cellular participation during ischemia and reperfusion injury, there may be similarities in the underlying mechanism. IL-1 is recognized as an early stage mediator of organ injury, and may be generated by resident or newly infiltrated inflammatory cells giving rise to organ specific tissue pathology.

Current research in ischemia related brain disorders implicates enhanced synaptic release of excitatory amino acid neurotransmitters as a major contributor to brain injury. However, recent animal studies also suggest a possible role for certain cytokines as described, for example, in Relton & Rothwell, *Brain Res. Bull.*, 29:243–246 (1992). In addition, increased levels of IL-1β in cerebralspinal fluid have been detected in pathophysiological conditions including chronic relapsing experimental encephalomyelitis in guinea pig, bacterial meningitis in humans, patients with human immunodeficiency virus type-1 infection, Alzheimer's disease and in patients with head injuries. Furthermore, it has also been found that recombinant human IL-1β when injected into the striatum of rats produced extensive neuronal damage with a loss of glutamic acid decarboxylase activity as described in Rothwell & Relton, *Neurosci. Biobehav. Rev.*, 17:217–227 (1993). These studies indicate the involvement of the IL-1 receptor systems in the pathogenesis of ischemia related brain disorders, including cerebral palsy.

Cerebral palsy is a generic term defining a non-progressive static disturbance of motor function, present from birth or early life, caused by a discrete encephaloclastic insult to the central nervous system (CNS) during gestation, the perinatal period or infancy. Although most cases result from ischemic-hypoxic insults, infection, hemorrhage or trauma may occasionally result in the pathologic condition.

The lesions associated with cerebral palsy are predominantly caused by ischemic-hypoxic insults to the immature brain due to asphyxia. There are several types of cerebral palsy depending on the pattern, location and severity of the ischemic-hypoxic insult. For example, spastic diplegia results from ischemic-hypoxia necrotic lesions localized near the dorsolateral surfaces of the lateral ventricles believed to be an end-arterial zone in pre-term infants. More extensive ischemic-hypoxic insults produce significant cystic destruction of central white matter of the hemispheres (deep lesions) associated with quadriplegia and mental deficiency. Ischemic-hypoxic insults to term infants tend to affect the parasagittal and parietoccipital cortex watershed zone, hippocampus, thalamus, and cerebellar hemispheres (superficial lesions). Congenital hemiplegia results from arterial occlusion in the middle cerebral artery territory resulting in a pro-encephalic lesion of the hemisphere, or from a more diffuse and partial hemisphere insult. The extent of damage to the cerebral cortex has been correlated with an increased likelihood of seizures and abnormal intelligence. There are no known effective methods for treating cerebral palsy.

Multiple sclerosis (MS) is an inflammatory demyelinating disease of the CNS. MS is a progressive disease of adults characterized by relapses and remissions, often leading to progressive physical, cognitive and emotional impairment. Although the cause of MS is unknown, the pathological, genetic and immunological features of the condition have been identified and indicate that the disease has an autoimmune basis.

Studies have shown that IL-1 can augment the in vitro activation of encephalitogenic T lymphocytes and enhance adoptive transfer of experimental autoimmune encephalomyelitis (EAE). EAE is an acute or chronic relapsing inflammatory demyelinating disease of the CNS resulting from sensitization of genetically susceptible animals with neuroantigens such as myelin basic protein (MBP). EAE is an art-accepted and often used animal model for acute human MS. Evidence of the involvement of IL-1 in immune-mediated demyelination comes from in vivo EAE studies. These studies demonstrate that exogenous IL-1α can exacerbate the clinical severity and duration of the paralysis observed in the EAE animal model. Current treatment for MS include the use of steriods and more recently interferon β (IFβ). Steriods, however, are known to have many deleterious side effects when administered over a period of time.

Accordingly, a need exists for an effective, yet selective, inhibitor or IL-1 for the treatment, amelioration or prevention of arthritis, IBD, sepsis and septic shock, ischemic injury, reperfusion injury, multiple sclerosis and ischemic brain injury such as cerebral palsy and generally for use in the treatment of inflammation. The present invention satisfies this need and provides related advantages as well.

SUMMARY OF THE INVENTION

The present invention relates to methods of treating or preventing IL-1 mediated diseases by administering to a patient in need thereof a therapeutic amount of an IL-1 inhibitor to prevent, treat or ameliorate IL-1 mediated diseases. Such IL-1 mediated diseases include, for example, arthritis, inflammatory bowel disease, sepsis and septic shock, ischemic injury, reperfusion, ischemic brain injury such as cerebral palsy and multiple sclerosis.

Particularly useful IL-1 inhibitors are proteins, and more particularly, naturally-occurring proteins since they pose a relatively low risk of producing undesirable or unforeseen side effects in patients treated with the IL-1 inhibitor. Preferably, the IL-1 inhibitors are the human proteins that naturally serve as IL-1 receptor antagonists (IL-1ra's). Also preferred are proteins that have been modified from such naturally-occurring IL-1ra's, for example by the addition of polyethylene glycol (PEG) or any other repeat polymer to increase their circulating half-life and/or to decrease their immunogenicity. In addition, the proteins can be modified by addition, deletions or substitutions in the amino acid sequence of such IL-1ra's that does not substantially reduce the biological activity of the unmodified protein.

DETAILED DESCRIPTION OF THE INVENTION

Figure 1:
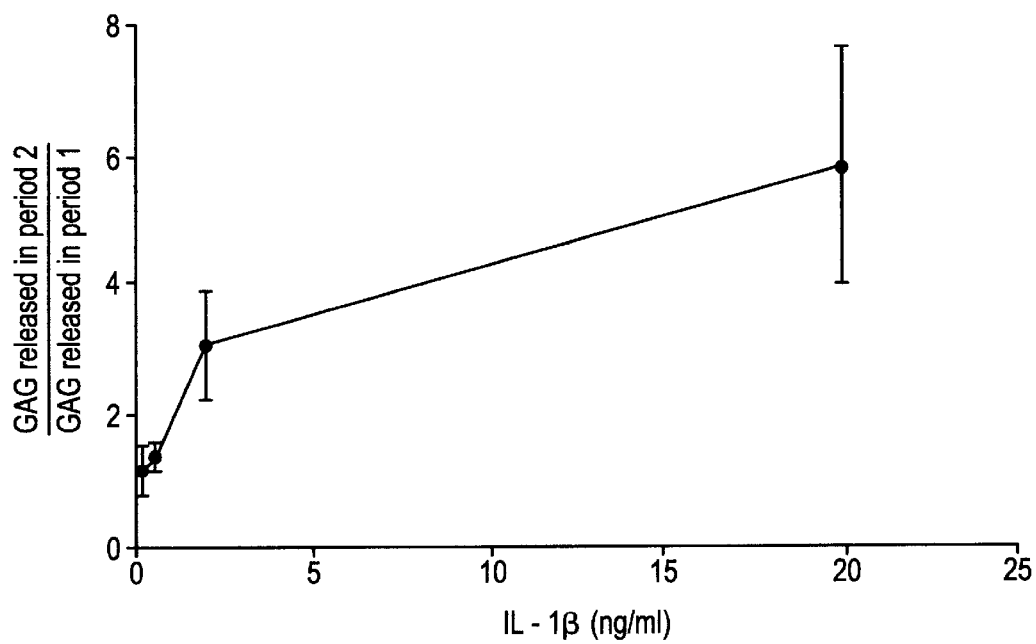
FIG. 1 shows the release of glycosaminoglycans (GAG) from bovine nasal cartilage in response to increasing amounts of IL-1β.

The present invention relates to methods for treating or preventing various IL-1 mediated conditions. Such conditions include, for example, arthritis, inflammatory bowel disease, sepsis including septic shock, ischemic injury, reperfusion injury, ischemic brain injury such as cerebral palsy and multiple sclerosis. Other IL-1 mediated diseases include osteoporosis, asthma, insulin diabetes, myelogenous and other leukemias, psoriasis, and cachexia/anorexia. These methods are accomplished by administering a therapeutically effective amount of an IL-1 inhibitor to a patient in need thereof.

In one embodiment, the IL-1 inhibitors of the present invention are naturally-occurring proteins that serve as IL-1 receptor antagonists. These naturally-occurring proteins are particularly useful in part because they pose a comparatively low risk of producing unforeseen and undesirable physiological side effects in treated patients.

For purposes herein, a protein is deemed to be "naturally-occurring" if it or a substantially equivalent protein can be found to exist normally in healthy humans or other animals. "Naturally-occurring" proteins can be obtained by recombinant DNA methods as well as by the isolation of the proteins from cells that ordinarily produce them. Thus, "naturally occurring" also encompasses proteins that contain an N-terminal methionyl group as a consequence of expression in procaryotic cells, such as $E.$ $coli.$ "Substantially equivalent" as used herein is defined to mean possessing a very high degree of amino acid residue homology (see generally, M. Dayhoff, $Atlas$ $of$ $Protein$ $Sequence$ $and$ $Structure,$ 5:124 (1974), specifically incorporated herein by reference), as well as possessing comparable biological activity to the naturally-occurring proteins. By "biologically equivalent", as used throughout the specification and claims, we mean compositions of the present invention that are capable of preventing IL-1 action in similar fashion, but not necessarily to the same degree, as the native IL-1 inhibitor isolated from monocytes. By "substantially homologous", as used throughout the ensuing specification and claims, is meant a degree of homology to the native IL-1 inhibitor isolated from monocyte-conditioned medium in excess of that displayed by any previously reported IL-1 inhibitors. Preferably, the degree of homology is in excess of 70 percent, more preferably in excess of 80 percent and even more preferably in excess of 90 percent. A particularly preferred group of inhibitors is in excess of 95 percent homologous with the native inhibitor. The percentage homology as described is calculated as the percentage of amino acid residues found in the smaller of the two sequences that align with identical amino acid residues in the sequence being compared when four gaps in a length of 100 amino acids may be introduced to assist in that alignment as set forth by Dayhoff, M. D. in Atlas of Protein Sequence and Structure, Vol. 5, p.124 (1972), National Biochemical Research Foundation, Washington, D.C., specifically incorporated herein by reference.

Particularly preferred IL-1ra's of the present invention are the naturally-occurring proteins that exist in vivo as regulators of IL-1 that have previously been described in U.S. Pat. No. 5,075,222 entitled "Interleukin-1 Inhibitors" (referred to herein as the '222 patent) which is incorporated herein by reference in its entirety. The proteins include glycosylated as well as non-glycosylated IL-1 receptor antagonists.

Three useful forms of Il-1ra are disclosed and described in the '222 patent. The first of these, IL-1ra$\alpha$, is characterized as a 22–23 kD molecule on SDS-PAGE with an approximate isoelectric point of 4.8, eluting from a Mono Q FPLC column at around 52 mM NaCl in Tris buffer, pH 7.6. The second, IL-1ra$\beta$, is characterized as a 22–23 kD protein, eluting from a Mono Q column at 48 mM NaCl. Both Il-1ra$\alpha$ and IL-1ra$\beta$ are glycosylated. The third, IL-1rax, is characterized as a 20 kD protein, eluting from a Mono Q column at 48 mM NaCl and is non-glycosylated. All three of these inhibitors were shown to possess similar functional and immunological activities. As disclosed in the '222 patent, the amino acid sequence of IL-1ra is as follows:

(U)(X) Pro Ser Gly Arg Lys Ser Ser Lys Met Gln Ala Phe Arg Ile Trp Asp Val Asn Gln Lys Thr Phe Tyr Leu Arg Asn Asn Gln Leu Val Ala Gly Tyr Leu Gln Gly Pro Asn Val Asn Leu Glu Glu Lys Ile Asp Val Val Pro Ile Glu Pro His Ala Leu Phe Leu Gly Ile His Gly Gly Lys Met Cys Leu Ser Cys Val Lys Ser Gly Asp Glu Thr Arg Leu Gln Leu Glu Ala Val Asn Ile Thr Asp Leu Ser Glu Asn Arg Lys Gln Asp Lys Arg Phe Ala Phe Ile Arg Ser Asp Ser Gly Pro Thr Thr Ser Phe Glu Ser Ala Ala Cys Pro Gly Trp Phe Leu Cys Thr Ala Met Glu Ala Asp Gln Pro Val Ser Leu Thr Asn Met Pro Asp Glu Gly Val Met Val Thr Lys Phe Tyr Phe Gln Glu Asp Glu wherein (U) is nothing, Met or comprises an N-terminal secretion leader sequence which directs the polypeptide out of a cell in a processed form and (X) is Arg or Pro.

Methods for producing the IL-1 inhibitors are also disclosed in the '222 patent. One disclosed method consists of isolating the inhibitors from human monocytes, where they are naturally produced. A second disclosed method involves isolating the gene responsible for coding the inhibitors, cloning the gene in suitable vectors and cells types, expressing the gene to produce the inhibitors and harvesting the inhibitors. The latter method, which is exemplary of recombinant DNA methods in general, is a preferred method of the present invention. Recombinant DNA methods are preferred in part because they are capable of achieving comparatively greater amounts of protein at greater purity.

The present invention also includes modified IL-1ra's. In one embodiment, the Il-1ra is modified by attachment of one or more polyethylene glycol (PEG) or other repeating polymeric moieties as described in PCT Publication No. WO 92/16221, specifically incorporated herein by reference. In another embodiment, the IL-1ra contains an N-terminal methionyl group as a consequence of expression in $E.$ $coli.$ Additional IL-1 inhibitors include compounds capable of specifically preventing activation of cellular receptors to IL-1. Such compounds include IL-1 binding proteins such as soluble receptors and antibodies, including monoclonal antibodies. Such compounds also include receptor antagonists and monoclonal antibodies to the receptors.

A second class of IL-1 inhibitors include the compounds and proteins that block in vivo synthesis and/or agents that affect transcription of IL-1 genes or processing IL-1 preproteins. Under certain conditions, the IL-1 inhibitor will block IL-1 induced IL-1 production.

Preferably, the above described IL-1ra's are produced by the aforementioned method in "substantially pure" form. By "substantially pure" it is meant that the inhibitor, in an unmodified form, has a comparatively high specific activity, preferably in the range of approximately 150,000–500,000 receptor units/mg as defined in Hannum et al., *Nature*, 343:336–340 (1990); and Eisenberg et al., *Nature*, 343:341–346 (1990), both of which are specifically incorporated herein by reference. It is to be recognized, however, that derivatives of IL-1ra can have different specific activities. In a preferred embodiment of the present invention, a therapeutic composition comprising at least one IL-1ra is administered in an effective amount to patients suffering from an interleukin-1 mediated disease.

Because it is possible that the inhibitory function of the IL-1 inhibitors is imparted by one or more discrete and separable portions, it is also envisioned that the method of the present invention could be practiced by administering a therapeutic composition whose active ingredient consists of that portion (or those portions) of an inhibitor which controls (or control) IL-1 inhibition.

The therapeutic composition of the present invention is preferably administered parenterally by injection, although other effective administration forms, such as intraarticular injection, inhalant mists, orally active formulations, or suppositories, are also envisioned. One preferred carrier is physiological saline solution, but it is contemplated that other pharmaceutically acceptable carriers may also be used. In one preferred embodiment, it is envisioned that the carrier and the IL-1ra constitute a physiologically-compatible, slow-release formulation. The primary solvent in such a carrier may be either aqueous or non-aqueous in nature. In addition, the carrier can contain other pharmacologically-acceptable excipients for modifying or maintaining the pH, osmolarity, viscosity, clarity, color, sterility, or odor of the formulation. Similarly, the carrier can contain still other pharmacologically-acceptable excipients for modifying or maintaining the stability, rate of dissolution, release or absorption of the IL-1ra. Such excipients are those substances usually and customarily employed to formulate dosages for parenteral administration in either unit dose or multi-dose form.

Once the therapeutic composition has been formulated, it can be stored in sterile vials as a solution, suspension, gel, emulsion, solid, or dehydrated or lyophilized powder. Such formulations can be stored either in a ready to use form or requiring reconstitution immediately prior to administration. The preferred storage of such formulations is at temperatures at least as low as 4° C. and preferably at −70° C. It is also preferred that such formulations containing IL-1ra are stored and administered at or near physiological pH. It is presently believed that storage and administration in a formulation at a high pH (i.e., greater than 8) or at a low pH (i.e., less than 5) is undesirable.

Preferably, the manner of administering the formulations containing IL-1ra is via an intraarticular, subcutaneous or intramuscular route. Preferably, the manner of administering the formulations containing IL-1ra is via intra-articular, subcutaneous, intramuscular or intravenous injection, suppositories, enema, inhaled aerosol, or oral or topical routes. To achieve and maintain the desired dose of IL-1ra, repeated subcutaneous or intramuscular injections can be administered. Both of these methods are intended to create a preselected concentration range of IL-1ra in the patient's blood stream. Preferably, circulating concentrations of Il-1ra range from 0.01 ng/ml to about 100 µg/ml.

A preferred dosage range for the treatment of interleukin-1 mediated arthritis is between 1 and 100 ng/ml. Accordingly, dosages are initially administered to bring the circulating levels of IL-1ra above 10 ng/ml of plasma and that, thereafter, doses are administered at a suitable frequency to keep the circulating level of IL-1ra at or above approximately 10 ng/ml of plasma. The frequency of dosing depends on the pharmacokinetic parameters of the IL-1ra in the formulation used.

A preferred dosage range for the treatment of IL-1 mediated IBD is between about 0.5–50 mg/kg of patient weight administered between about 1 and 10 times per day. More preferably, the dosage is between about 1–10 mg/kg of patient weight administered between about 3 and 5 times per day. The frequency of dosing depends on the pharmacokinetic parameters of the IL-1ra in the formulation used.

A preferred dosage range for the treatment of IL-1 mediated sepsis and septic shock is between about 1.0–200 mg/kg per day of patient body weight per 24 hours administered in equal doses between about 4–15 times per 24 hours. In a more preferred embodiment, the dosage is between about 10–120 mg/kg per day of patient body weight administered in equal doses every 24 hours. In the most preferred embodiment, 100 mg/kg of patient body weight per 24 hours is equally administered every 2 hours. The frequency of dosing depends on the pharmacokinetic parameters of the IL-1ra in the formulation used.

In an additional preferred mode for the treatment of IL-1 mediated sepsis and septic shock, an initial bolus injection of IL-1ra is administered followed by a continuous infusion of IL-1ra until circulating IL-1 levels are no longer elevated. The goal of the treatment is to maintain serum IL-1ra levels between 2–20 µg/ml for this period. In a preferred embodiment of this mode, an initial bolus of IL-1ra is administered followed by the continuous administration of IL-1ra of between about 5–20 µg/kg of patient body weight per minute until circulating IL-1 levels are not longer elevated. Serum IL-1β levels may be ascertained by commercially available immunoassay test kits. The initiation of treatment for IL-1 mediated sepsis and septic shock should be begun, under either mode of treatment, as soon as possible after septicemia or the chance of septicemia is diagnosed. For example, treatment may be begun immediately following surgery or an accident or any other event that may carry the risk of initiating sepsis or septic shock.

A preferred dosage range for the treatment of IL-1 mediated ischemia and reperfusion injury is between about 1–50 mg/kg of patient weight administered hourly. In a preferred embodiment, an initial bolus of about 15–50 mg/kg of IL-1ra is administered, followed by hourly injections of about 5–20 mg/kg. The frequency of dosing depends on the pharmacokinetic parameters of the IL-1ra in the formulation used.

A preferred dosage range for the treatment of IL-1 mediated multiple sclerosis is between about 10–100 mg/kg administered to maintain a blood level of circulating IL-1ra levels between 2–20 µg/ml for the length of the relapse. The frequency of dosing depends on the pharmacokinetic parameters of the IL-1ra in the formulation used.

A preferred dosage range for the treatment of IL-1 mediated cerebral infarctions such as cerebral palsy is between about 10–100 mg/kg by infusion to sustain a high level of IL-1ra levels at 2–20 µg/ml. The frequency of dosing depends on the pharmacokinetic parameters of the IL-1ra in the formulation used.

It is also contemplated that certain formulations containing IL-1ra are to be administered orally. Preferably, IL-1ra is encapsulated for oral administration. The encapsulated IL-1ra can be formulated with or without those carriers and excipients customarily used in the compounding of solid dosage forms. Preferably, the capsule is designed so that the active portion of the formulation is released at that point in the gastrointestinal tract when bioavailability is maximized and pre-systemic degradation is minimized. Additional excipients can be included to facilitate absorption of the IL-1ra as well as diluents, flavorings, low melting point waxes, vegetable oils, lubricants, suspending agents, tablet disintegrating agents and binders.

When used for the treatment of IL-1 mediated IBD, the administration of IL-1ra can also be accomplished in a suitably formulated enema.

Regardless of the manner of administration, the specific dose is calculated according to the approximate body weight or surface area of the patient. Other factors in determining the is appropriate dosage can include the disease or condition to be treated or prevented, route of administration and the age, sex and medical condition of the patient. Further refinement of the calculations necessary to determine the appropriate dosage for treatment involving each of the above mentioned formulations is routinely made by those of skilled in the art and is without undue experimentation, especially in light of the dosage information and assays disclosed herein. These dosages can be determined through the use of known assays for determining dosages used in conjunction with appropriate dose-response data.

The pharmaceutical compositions of the present invention can be used for veterinary as well as human applications. Accordingly, the term "patient" is intended to encompass animals as well as humans.

The following examples are intended to illustrate, but not limit, the present invention.

EXAMPLE 1

Effects of Human IL-1 Inhibitor on Cultured Bovine Nasal Cartilage Explant

Numerous in vitro and in vivo methods have been used to study the progression of arthritis. One in vitro model which has proven to be especially useful in this regard is cultured cartilaginous tissue explant. In fact, this model has been used in the past to demonstrate that IL-1 is a powerful mediator of cartilage destruction and, therefore, a propitious target for intervention in arthritic joint erosion. (See generally, G. Buchan et al., Third Annual General Meeting of the British Society for Rheumatology, London, England, Nov. 19–21, 1988, *PR. J. Rheumatology,* Supplement 2 (1986); Fontana et al., *Rheumatol. Int.* 2:49–53 (1982); J. Saklatvala et al., *Development of Diseases of Cartilage and Bone Matrix,* pp. 291–298 (Alan R. Liss); P. Stashenko et al., *The American Association of Immunologists,* 138:1464–1468 (1987); Dodge et al., *J. Clin. Invest.,* 83:647–661; J. Sandy et al., *J. Orthopedic Res.,* 4:263–272; Saklatavala et al., *The Control of Tissue Damage* pp. 97–108 (Elsevier Science Publ.); Campbell et al., *Biochem. J.,* 237:117–122; Tyler, *Biochem. J.,* 225:493–507; and Eastgate et al., Sixth International Lymphokine Workshop, 7(3):338).

The cartilage explant model essentially as described by Steinberg et al., *Biochem. J.,* 180:403–412, incorporated herein by reference, was used in the experiments reported in this Example to demonstrate the mitigating effect of IL-1ra on IL-1 mediated cartilage breakdown. While bovine nasal septum was used here as the source of cartilaginous tissue, articular cartilage of the type described in Typer et al., *Br. J. Theumatol.,* 24(1):150–155, incorporated herein by reference, can also be used.

A. Preparation of Cartilage

Bovine nasal septum was removed from freshly sacrificed yearling steers and placed on ice. The tissue was then scrubbed with Povidone-Iodine prep solution (1-ethanol-2-pyrolidinone homopolymer with iodine, obtained from Medline Industries (Mundelein, Ill.). The mucosa and perichondrium were then removed. The remaining cartilaginous septum was then immersed in a 5% (v/v) solution of Povidone/Iodine for one hour at room temperature.

The following procedures were then performed aseptically in a laminar flow hood. The septa were repeatedly rinsed with Grey's Balanced Salt Solution (GIBCO laboratories, Grand Island, N.Y.). The cartilage sheet was then placed on a sterile surface, and uniform 8 mm plugs were removed using a standard cork borer. Approximately 1–2 mm of the top and bottom surfaces were removed using a razor blade. The plugs were then held in the Grey's Balanced Salt Solution. Plugs taken from different steers were kept separately.

Each plug was then sectioned into several 0.8 mm disks. The cutting device used was an aluminum block of the type described by Steinberg et al., *Biochem. J.,* 180:403–412. The disks produced were consistently between 40 and 50 mg wet weight. The disks were kept in culture in Delbecco's Modified Eagle Medium (DMEM) plus 10% fetal calf serum, plus penicillin, streptomycin and neomycin, hereinafter referred to as the "medium." The cultures were maintained in a 37° C. incubator with 5% $CO_2$.

Representative disks from each steer were then tested for their ability to respond to IL-1β as indicated by the release of glycosaminoglycans (GAG) into the culture medium. Glycosaminoglycans are released from a cell once the cell matrix has been degraded. The presence of GAG was detected using 1, 9-dimethylenethylene blue as described by Ferndale et al, *Connective Tissue Research,* 9:247–248, incorporated herein by reference. Disks that responded to 5 ng/ml of IL-1β by increasing output of GAG two fold or greater as compared to an unstimulated basal rate were selected for use in the following experiments. These disks are hereinafter referred to as "IL-1β responsive disks."

B. IL-1 Dose Response

This preliminary experiment was performed to determine whether a dose response curve exists to increasing amounts of IL-1β. First, several of the IL-1β responsive disks were sectioned into quarter slices. The remainder was set aside for later experiments. Because responses to IL-1 frequently vary from animal to animal, disk to disk, and slice to slice, the steps of this experiment were designed so that each slice served as its own control.

Second, each slice was incubated in one well of a 48 well tissue culture cluster (Costar, Cambridge, Mass.) with a constant volume of the previously described medium. After 48 hours, the amount of GAG present in the supernatant of each culture was measured. This amount was then normalized for each culture in terms of μg GAG per mg wet weight of tissue. In this manner, a basal rate of GAG release in the absence of IL-1 was established for each slice.

Third, the supernatants from all the cultures were discarded and replaced with fresh medium containing differing amounts of IL-1β. The IL-1β was produced in-house (J. Childs, notebook 935, pages 49–52) and after characterization, was utilized in all experiments calling for its use. After a 48 hour incubation with IL-1β, the supernatants from the cultures were recovered, and the amount of GAG present in each was measured. These amounts were normalized for each culture as above. The basal rates were then subtracted from the IL-1β induced rates. The results are reported in FIG. 1. As FIG. 1 clearly indicates, the release of GAG from the cartilaginous tissue is dependent on the amount of IL-1β administered.

Because 5 ng/ml of IL-1β caused an easily measurable increase in GAG release during the 48 hour period of culturing, this concentration was used in the following experiment.

C. Effects of rIL-1ra on IL-1 Induced GAG Release

Several of the remaining IL-1β responsive disks were next sectioned into quarter slices. As above, each slice was used as its own control.

Each slice was then incubated with a constant volume of the previously-described medium for 48 hours in a 48 well tissue culture cluster. A basal rate of GAG release was determined for each slice. Next, the supernatants from the cultures were discarded and replaced with fresh medium containing 5 ng/ml of IL-1β and differing amounts of recombinantly produced IL-1ra (rIL-1ra). After a 48 hour incubation, the supernatants were recovered, and the amounts of GAG were measured. These amounts were normalized for each culture by dividing the rIL-1ra/IL-1β stimulated GAG release rate by the basal GAG release rate. The results are summarized in Table 1. In all cases the concentration of IL-1β is 5 ng/ml (n=6).

TABLE 1

THE EFFECT OF RECOMBINANT IL-1ra ON IL-1β INDUCED DEGRADATION OF BOVINE NASAL CARTILAGE

| [IL-1ra] | [IL-1ra]/[IL-1β] | Fold Stimulation period II/periodI (+/−standard deviation) |
|---|---|---|
| 0 | | 4.02 ± 1.7 |
| 5 ng/ml | 1 | 2.4 ± 0.47 |
| 10 ng/ml | 2 | 1.7 ± 0.4 |
| 25 ng/ml | 5 | 1.3 ± 0.4 |
| 50 ng/ml | 10 | 1.0 ± 0.2 |
| 150 ng/ml | 30 | 1.1 ± 0.2 |

The results show that the release of GAG from cartilaginous tissue was sharply curtailed by an increase in the concentration of rIL-1ra relative to that of IL-1β. For instance, a ten times molar excess of rIL-1ra over IL-1β (the molecular weights of IL-1β and rIL-1ra are both approximately 17 kD) was sufficient to return the GAG release rate to the basal level. Similarly, a 1.5 times molar excess of rIL-1ra over IL-1β was sufficient to reduce the stimulation of GAG release to 50% of that observed in the presence of IL-1β alone. These results were reproduced using cartilage derived from several different steer.

D. Lack of Cytotoxicity of rIL-1ra

To show that rIL-1ra is noncytotoxic, slices from the remaining IL-1β responsive disks were exposed to varying amounts of rIL-1ra in the absence of IL-1β. The rate of GAG release was the same as when neither rIL-1ra nor IL-1β was present.

Next, to show that the effects of IL-1ra are reversible, rIL-1ra was removed from the supernatants of culturing slices and IL-1β was added. The slices responded as they did in the IL-1β dose response experiment. Similar results occurred when cartilage that had been treated with IL-1β and a sufficient concentration of rIL-1ra to completely block the action of IL-1β was subsequently exposed to IL-1β alone.

EXAMPLE 2

Effects of IL-1ra on Collagen-Induced Arthritis in Mice

Type II collagen-induced arthritis in mice bears many resemblances to human rheumatoid arthritis and has been used for several years to study certain aspects of that disease (Stuart et al., FASEB J., 2(14):2950–2956 (1988)). The potential involvement of IL-1 in rheumatoid arthritis has been noted by Stimpson et al., J. Immunol., 140:2964–2969 (1988).

The purpose of this experiment was to demonstrate that systemic administration of rIL-1ra has a mitigating effect on the pathogenesis of type II collagen-induced arthritis in mice.

Twenty-four mice DBA/1 mice, purchased from Jackson Laboratories, were immunized with 0.1 mg chick type II collagen in Freund's complete adjuvant. At day 14 post immunization, the animals were randomly subdivided into two groups of twelve animals each. The experimental group was injected intraperitoneally twice daily with approximately 0.1 mg rIL-1ra/kg/injection. The injections continued until the animals were sacrificed at day 47 post immunization (i.e., after 34 days of dosing). Control animals were injected with an equal volume of vehicle (10 mM sodium phosphate, 150 mM sodium chloride) on the same schedule.

Figure 2:
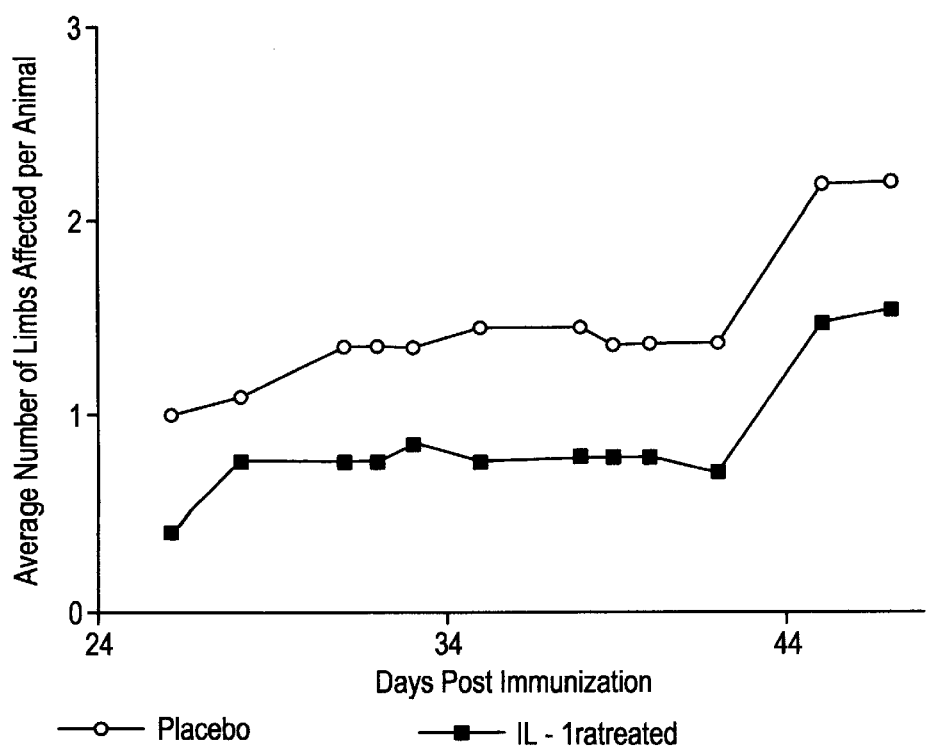
FIGS. 2 and 3 depict the inhibitory effect of IL-1ra on the pathogenesis of type II collagen-induced arthritis in mice.
Figure 3:
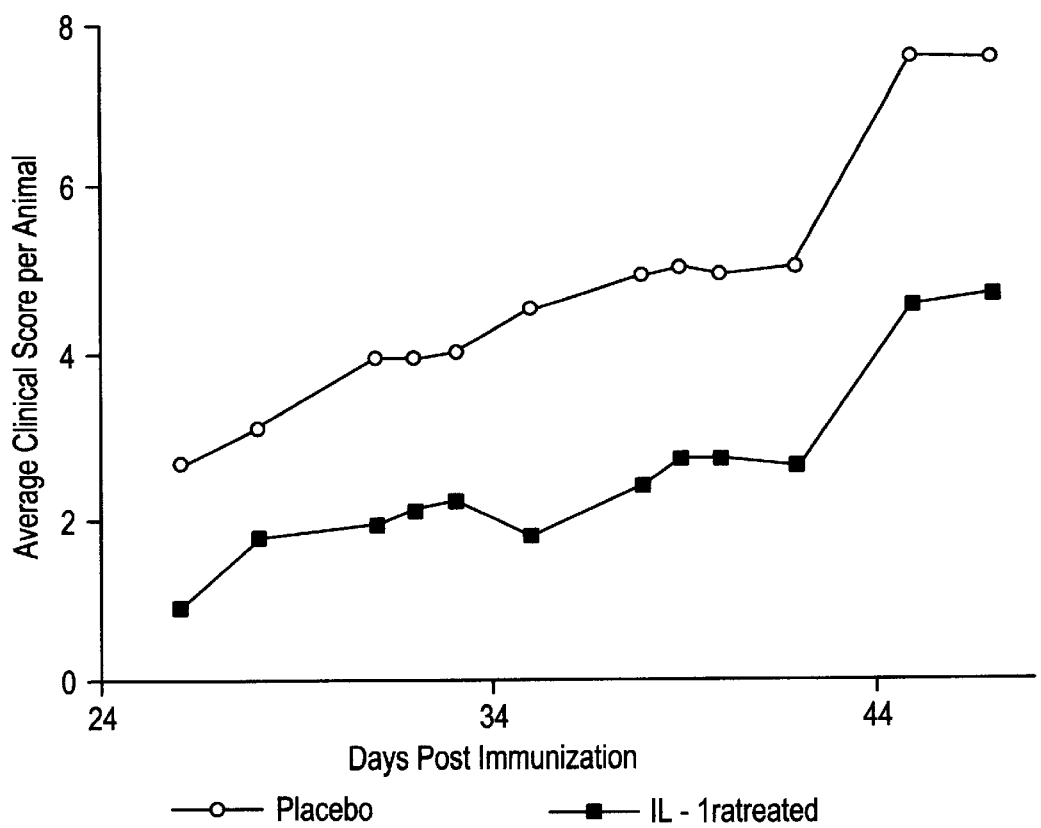

Affected limbs were counted and clinical scoring was performed approximately three times weekly during the in-life portion of the experiment. Clinical scores from each animal represent, on a 0–4 point basis, the severity of arthritis sustained by each paw as assessed by blinded observers. The clinical scores for each animal from day 26, when the first signs of clinically observable arthritis were noted, through day 47, when the animals were sacrificed. These results are graphed as a function of time in FIGS. 2 and 3, respectively. As can clearly be seen, the incidence and severity of the disease were slowed down considerably by the administration of rIL-1ra.

EXAMPLE 3

Effects of Human IL-1 Inhibitor on Streptococcal Cell Wall-Induced Reactivation of SCW-Induced Arthritis in Rats Regarding streptococcal cell wall-induced arthritis, R. L. Wilder in *Immunopathogenetic Mechanisms of Arthritis*, Chapter 9 entitled "Experimental Animal Models of Chronic Arthritis" comments "the clinical, histological and radiological features of the experimental joint diseases closely resemble those observed in adult and juvenile rheumatoid arthritis."

The experiments described below employs the model disclosed in Esser et al., *Arthritis and Rheumatism*, 28:1401–1411 (1985), specifically incorporated herein by reference. Briefly, streptococcal cell wall (SCW) is injected intraarticularly into the ankle joint of Lewis rats. Saline is injected into the contralateral joint to provide a control. After a period of twenty days, in which the initial inflammation dies away, SCW is again administered, this time by intravenous injection. This dose of SCW is insufficient to cause joint inflammation by itself and, therefore, has little or no effect on the saline injected ankle. However, this dose is capable of reactivating inflammation and joint destruction in the ankle previously injected with SCW. To assess the extent of inflammation following the second administration of SCW, the dimensions of the ankle joint are measured daily.

In one of many experiments performed with the above described model, two groups of twelve rats were used. Each animal was injected in the right ankle with SCW (1.8 μg rhamnose equivalence) and in the left ankle with an equal volume of pyrogen-free saline. Ankle dimensions were measured on days 1 through 6.

On day 20, one group of rats was injected intraperitoneally with 1 mg/kg IL-1ra in an aqueous vehicle; the other group was injected intraperitoneally with an equal volume of the vehicle solution only. One hour later, each animal was injected intravenously with SCW (100 μg rhamnose equivalence). Ten minutes later, the treatment group was injected intraperitoneally with 1 mg/kg IL-1ra, and the control group was injected with vehicle alone. Subcutaneous injections of IL-1ra at 1 mg/kg were given at 2 and 6 hours post SCW administration and were repeated every 6 hours thereafter for the next 3 days.

Table 2 shows the dimensions of the saline injected and SCW injected ankles for both the treatment group and the control group over the course of the experiment.

TABLE 2

ANKLE JOINT DIAMETER OF RATS INJECTED WITH SCW AND TREATED WITH IL-1ra OR SALINE ACCORDING TO PROTOCOL IN EXAMPLE 3

Joint Diameter (mm) (±SD)

| | SCW Injected Joints | | | | Saline Injected Joints | | | |
|---|---|---|---|---|---|---|---|---|
| Day | IL-1ra | SD | Saline | SD | IL-1ra | SD | Saline | SD |
| 0 | 5.96 | .12 | 6.02 | .10 | 5.95 | .17 | 5.96 | .16 |
| 1 | 7.95 | .33 | 7.73 | .36 | 5.94 | .15 | 5.94 | .13 |
| 2 | 7.44 | .28 | 7.42 | .27 | 5.98 | .11 | 5.95 | .17 |
| 3 | 7.20 | .39 | 7.23 | .27 | 6.00 | .12 | 6.01 | .07 |
| 6 | 6.78 | .27 | 6.64 | .29 | 6.06 | .09 | 6.06 | .13 |
| 10 | 6.58 | .34 | 6.63 | .18 | 6.00 | .12 | 5.85 | .16 |
| 14 | 6.44 | .21 | 6.36 | .17 | 5.99 | .08 | 5.90 | .17 |
| 20 | 6.46 | .18 | 6.52 | .14 | 5.91 | .11 | 5.87 | .20 |
| 21 | 7.34 | .36 | 7.78 | .31 | 5.73 | .18 | 5.78 | .12 |
| 22 | 8.31 | .58 | 8.70 | .43 | 5.85 | .16 | 5.96 | .22 |
| 23 | 8.55 | .81 | 9.06 | .42 | 6.02 | .19 | 5.99 | .16 |
| 24 | 8.23 | .71 | 8.56 | .39 | 6.03 | .13 | 5.94 | .20 |
| 25 | 8.00 | .56 | 8.16 | .43 | 6.05 | .12 | 6.06 | .17 |
| 28 | 7.48 | .40 | 7.71 | .30 | 6.04 | .13 | 5.98 | .13 |

As expected, the SCW treated ankles in both groups swelled in response to the intravenous injection of SCW. However, the response differed between treatment groups. The ankles in the control group swelled by about 30% of their initial dimensions over the first 3 days, whereas the ankles in the treatment group swelled only by 14% over the same period. Moreover, on days 1 through 5 post-intravenous injection of SCW, there was a statistically significant ($p<0.001$ by a two-tailed t-test for independent means) difference in the dimensions of the SCW-treated and contralateral control ankles of both groups.

On day 8, the rats were sacrificed and both ankles were fixed in formalin. The fixed joints were decalcified, stained, and examined. Significant differences in cartilage erosion, bursitis, periostitis, and synovitis were found between the control group and the treatment group. Some of these differences are set forth in Table 3.

TABLE 3

EFFECTS OF IL-1ra ON JOINT HISTOPATHOLOGY FOLLOWING SCW REACTIVATION OF JOINT INFLAMMATION (1 mg/kg 4 times daily on day 20 through 23)

| | Placebo Group | | IL-1ra Group | | |
|---|---|---|---|---|---|
| Pathology | Positives/12 | Score | Positives/12 | Score | P |
| Cartilage Erosion | 10 | 1.0 ± .6 | 3 | 0.25 ± .45 | .0023 |
| Bone Erosion | 3 | 0.25 ± .45 | 2 | 0.17 ± .39 | NS |
| Bursitis | 11 | 0.92 ± .29 | 3 | 0.25 ± .45 | .0003 |
| Periostitis | 9 | 0.75 ± .45 | 12 | 0.25 ± .45 | .013 |
| Synovitis | 12 | 2.21 ± .84 | 12 | 1.08 ± .47 | .00052 |
| PMN | 12 | 1.0 | 12 | 1.0 | NS |

EXAMPLE 4

Effects of Human IL-1 Inhibitor on Formalin-Immune Complex Induced IBD

The rabbit model of formalin-immune complex IBD has been used to investigate the role of arachidonic acid-derived inflammatory mediators and to evaluate therapeutic strategies in IBD. Zipser et al., supra; Brown et al., *Gastroenterology*, 92:45–59 (1987); Schumert et al., *Prostaglandins*, 36:565–577 (1988), all incorporated herein by reference.

The experiment described below employed the model disclosed in Zipser et al., supra. This model creates symptoms analogous to active ulcerative colitis, and is briefly summarized as follows: formaldehyde is administered via a catheter into the colon of rabbits and after a period of time the animals receive an injection of immune complexes in antigen excess. Time studies following the induction of IBD are conducted by sacrificing the animals after 48 hours and removing the colons. The colons are then histologically assessed. The effect of treatment with IL-1ra's prior to and after the induction of IBD on inflammation, edema and necrosis was compared with non-treated control animals.

A. Induction of IBD

Inflammation was induced in the distal colon of male New Zealand rabbits (2.2–2.5 kg) using a modification of the immune complex method of colitis described in Kirsnew et al., *Trans. Assoc. Am. Physicians*, 70:102–119 (1957); Hodgson et al., *Gut*, 19:225–32 (1978), which are incorporated herein by reference. Four ml of 0.45% (v/v) unbuffered formaldehyde (Electron Microscopy Sciences, Washington, Pa.) was administered via a catheter inserted 10 cm into the distal colon of anesthetized rabbits (xylazine and ketamine). Two hours later, animals received 0.85 ml of immune complexes in antigen excess through an ear vein. The complexes were prepared by incubating human serum albumin (500 μg/ml) with rabbit anti-human antisera (ICN Immunogiologicals, Costa Mesa, Calif.), decanting the supernatant, and redissolving the precipitated immune complexes with an albumin solution (6 mg/ml) as described in Zipser et al., supra.

Histologic evaluation was performed on a minimum of two longitudinal sections from each colon. All colon samples were examined in a blind fashion by a single pathologist. The mucosa and submucosa were separately evaluated for infiltration of acute inflammatory cells (neutrophils and eosinophils). A semiquantitative score of leukocytes (L) per high power field (HPF) was determined for each area examined using the following quantitations: 0=0 or 1; 0.5=2–9; 1=10–20; 1.5=21–30; 2=31–40; 2.5=

41–50; 3=51–65; 3.5=66–80; 4=>81 L/HPF. At a minimum, eight HPFs of mucosa and submucosa from each specimen were separately evaluated in each section. The inflammatory index was calculated by adding the averaged score for the mucosal and submucosal evaluations. Edema was semiquantitatively assessed on a scale of 0 to 4. Necrosis was expressed as the percent of mucosa involved. After the administration of formalin, followed by immune complexes, the distal colon develops acute inflammation. This inflammation is characterized by infiltration of neutrophils primarily into the mucosa and submucosa, mucus depletion, crypt abscesses, edema and scattered areas of mucosal necrosis, progressively increased from 0.3±0.1 (0 hours) to 4.5±0.7 (48 hours) (p<0.001), from 0.3±0.1 to 3.6±0.3 (p<0.001) and from 0% to 89% (p<0.001), respectively. A subsequent decrease in these parameters was observed 96 hours after the induction of IBD (p<0.01 versus 48 hours).

B. Treatment with IL-1ra's

A group of animals were treated intravenously with IL-1ra (5 mg/kg; n=8) or the vehicle alone (n=10) at six time points: 2 hours before and 1, 9, 17, 25, 33 hours after the administration of the immune complexes. The rabbits were sacrificed 48 hours after the induction of IBD and the colon tissue analyzed for inflammation.

Treatment of rabbits with IL-1ra significantly reduced inflammatory index from 3.2±0.4 to 1.4±0.3 (p<0.02), edema from 2.2±0.4 to 0.6±0.3 (p<0.01) and necrosis from 43±10% to 6.6±3.2% (p<0.03) compared to vehicle-treated IBD animals. This result shows that several of the indications of IBD may be significantly lessened by treatment with IL-1ra.

EXAMPLE 5

Bacterial Cell Wall Induced IBD in Rats

Unlike many other IBD models, the bacterial cell wall induced IBD model shows most of the indications for chronic IBD or Crohn's disease. In addition to the formation of chronic granulomatous response, this model is subject to spontaneous reactivation, anemia and extraintestinal inflammation.

The Bacterial Cell Wall model essentially as described by Sartor et al., supra., was used in this Example to demonstrate the mitigating affect of IL-1ra on IL-1 mediated IBD. The experiment was performed generally as follows: the IBD is induced in rats by the intravenous injection of a sterile sonicate of peptidoglycan polysaccharide from group A streptococci. Transient petechial hemorrhage of the colon appears within 2–3 minutes and resolves by 48–72 hours after injection. A sample group of animals were treated with IL-1ra following induction of IBD, and after a period of time the animals were sacrificed, the colons removed and gross pathology evaluated.

C. Induction of IBD

The bacterial cell wall material was prepared according to the procedures set forth in Stimpson et al., Infect. Immun. 51:240–249 (1986), incorporated herein by reference. Lewis rats are given subsercosal injections with streptococcal cell walls. The injections result in both local and systemic disorders that include bowel adhesions and nodules, an increased liver weight and hepatic nodules, a reduced hematocrit and hemoglobin level, and increased white blood cell count (WBC), a reduced growth rate, and a joint swelling characteristic of arthritis (see Sartor et al., Gastroenterology, 89:587–595 (1985), incorporated herein by reference). Three separate protocols for treatment with IL-1ra were performed with this model and reductions in nodules and adhesions have been observed in all of them. In the last two protocols, the reductions in adhesions were statistically significant.

D. Protocol A

Two groups of 12 rats were used. On day 1, both were injected with 15 µg total of streptococcal cell wall-derived peptidoglycan polysaccharide (SCW PG-APS), at 7 sites; 3 areas of the cecum, 2 areas of the Peyer's patches, and two areas of the ductal ileum. On day 11, overt signs of the disease appeared including joint swelling, diarrhea, and bloody nose. At this time, one group was dosed subcutaneously with IL-1 ra (8 mg/kg) every 12 hours and the second group was treated identically with placebo (PBS). On each day the size of the ankle joints were measured. On day 18, the animals were sacrificed and the intestines were scored on a scale of 0 to 4 for the presence of granulomas and adhesions (Table 4). The IL-1ra group had fewer nodules and adhesions. The IL-1ra group also had smaller livers as well as a reduced white blood cell count (WBC).

TABLE 4

EFFECTS OF IL-1ra ON SCW-INDUCED ENTEROCOLITIS IN THE RAT

|  | Intestinal Adhesions | Cecal Nodules | Liver Weight (gm) | WBC |
|---|---|---|---|---|
| IL-1ra | 1.7 | 1.8 | 16.9 | 48.8 |
| PBS | 2.2 | 2.4 | 18.6 | 57.7 |
| p value for comparison of groups | 0.14 | 0.10 | 0.19 | 0.13 |

E. Protocol B

The protocol was similar to that used in Protocol A except that the amount of PG-APS used was reduced to 12.5 µg and the treatment with IL-1ra was started at day 8. As in Protocol A, reductions in cecal nodules, intestinal adhesions, liver weights and WBC were observed (Table 5). The reduction in adhesion was significant at the p<0.02 level.

TABLE 5

EFFECTS OF IL-1ra ON SCW-INDUCED ENTEROCOLITIS IN THE RAT

|  | Intestinal Adhesions | Cecal Nodules | Liver Weight (gm) | WBC |
|---|---|---|---|---|
| IL-1ra | 1.4 | 1.7 | 13.3 | 35.1 |
| PBS | 2.2 | 2.3 | 14.1 | 35.8 |
| p value for comparison of groups | 0.017 | 0.077 | 0.23 | 0.43 |

F. Protocol C

The protocol used was again similar to that in Protocol A except that the amount of PG-APS was reduced to 12.5 µg (as in Protocol B) and the treatment group was started on IL-1ra 8 mg/kg subcutaneous (s.c.) and 2 mg/kg intravenously (i.v.) immediately following the PG-APS injection. Further IL-1ra injections (8 mg/kg) s.c. were given at 4, 10 and 18 hours on day 1, every 8 hours on day 2, and then every 12 hours for the duration of the experiment. Five animals in each group were sacrificed at day 3, and the remainder were sacrificed at day 18 for examination of gut lesions (Table 7).

TABLE 6

EFFECTS OF IL-1ra ON SCW-INDUCED ENTEROCOLITIS IN THE RAT

|  | Intestinal Adhesions | Cecal Nodules | Liver Weight (gm) | WBC |
|---|---|---|---|---|
| IL-1ra | 0.8 | 0.9 | 0.047 | 10.7 |
| PBS | 1.8 | 1.0 | 0.049 | 10.3 |
| p value for comparison of groups | 0.07 | 0.30 | 0.24 | 0.31 |

On day 3 there was a significant reduction in a global parameter representing gut lesions and a reduction in adhesions that approached significance (p=0.07). In the group sacrificed at day 18, the results were confused because no disease appeared in one of the animals in the control group. However, the reduction in adhesions in the IL-1ra group was still significant at the p<0.02 level and there was also a significantly greater weight gain in the IL-1ra group.

EXAMPLE 6

NSAID Induced IBD in Rats

Figure 4:
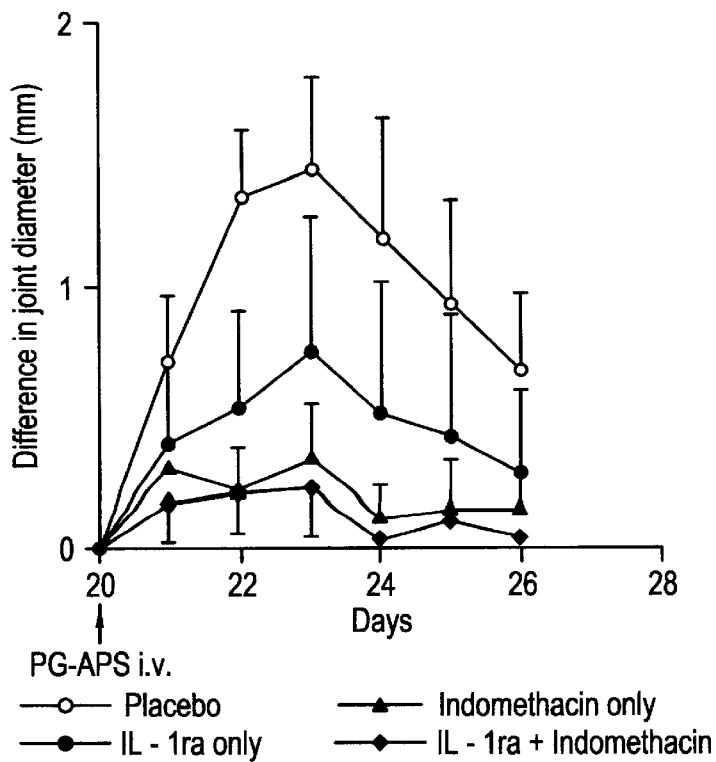
FIG. 4 depicts the effects of Il-1ra on PG-APS reactivation of joint inflammation in conjunction with indomethacin.

In an attempt to determine whether the anti-inflammation effects of IL-1ra would be additive with those of NSAIDs, rats were treated with indomethacin after the intravenous injection of PG-APS as described in Example 3 above (2 mg/kg at the time of reactivation at 12, 24 and 36 hours post activation, and every 12 hours up to 6 days), IL-1ra (2 mg/kg at 2 and 6 hours, then every 6 hours up to 36 hours and every 12 hours up to 7 days) or a combination of the two drugs as shown in FIG. 4. The group on indomethacin alone showed a greater reduction in joint swelling than that on IL-1ra alone. However, the indomethacin group was sick and two animals died during the course of the experiment. The group receiving both drugs did even better than the group on indomethacin alone; the joint swelling was less, and the difference between the two groups was statistically significant on day 4 at p<0.03 and on day 7 and 8 at p<0.06. No animals were sick in this group and there were fewer ulcerations in the mid small intestines. Ulceration of the mid small intestine is a complication in patients on chronic oral NSAIDs. It appears, therefore, that IL-1ra alleviates some of the IBD-like complications of NSAIDs.

Table 7 shows the effects of IL-1ra on both the intestinal symptoms—ulcers, adhesions, intestinal thickening and myleloperoxidase (MPO) levels—and systemic symptoms—hematocrit (HCT), hemoglobin (HgB) and WBC levels—associated with the NSAID treatment of PG-APS induced arthritis.

TABLE 7

EFFECTS OF IL-1RA TREATMENT ON INDOMETHACIN-INDUCED GUT INJURY IN THE RAT

| Treatment | Deaths | Ulcers # | Ulcers % Area | Adhesions | Intestinal Thickening | MPO u/g | HCT % | Hgb (g/dl) | WBC ($10^3/\mu l$) |
|---|---|---|---|---|---|---|---|---|---|
| Saline | 0/9 | 0 | 0 | 0/9 | 0/9 | 0.005(.001) | 42 | 15 | 6 |
| IL-1ra | 0/10 | 0 | 0 | 0/10 | 0/10 | 0.01(.01) | 41 | 14 | 8 |
| Indomethacin | 2/9 | 1.3(±0.6) | 7.1(±2.7) | 2/7 | 4/7 | 0.06(.02) | 37 | 13.5 | 11 |
| Indomethacin + IL-1ra | 0.8 | 0.6(±0.4) | 2.8(±1.9) | 3/8 | 2/8 | 0.03(.02) | 40 | 14 | 11 |

EXAMPLE 7

Effects of Human IL-1ra on Endotoxin Induced Septic Shock

Endotoxin induced septic shock studies were conducted on Blue Chinchilla rabbits. The experimental protocol did not focus on any indications for the induced septic shock other than group mortality. Rabbits were used in the study because their sensitivity to pyrogenic and metabolic effects of endotoxin and other bacterial products are similar to those of human subjects.

Shock was induced by a single intravenous injection of endotoxin time zero. The rabbits were given periodic intravenous injections into an ear vein at −10 minutes, at time zero, and for every two hours thereafter for a 24 hour period. The results of this study can be seen in Table 8.

TABLE 8

EXPERIMENTAL ENDOTOXIN INDUCED SHOCK IN RABBITS; EFFECTS OF IL-1ra ON SURVIVAL RATE

|  | survival (no) | | | | | survival rate |
|---|---|---|---|---|---|---|
|  | 12 h | 24 h | 36 h | 48 h | 7 d | 7 days (%) |
| A(N = 5) | 5 | 5 | 5 | 5 | 5 | 100 |
| B(N = 10) | 9 | 6 | 3 | 2 | 2 | 20 |
| C(N = 10) | 9 | 7 | 4 | 3 | 2 | 20 |
| D(N = 10) | 10 | 7 | 6 | 5 | 4 | 40 |
| E(N = 10) | 10 | 10 | 10 | 9 | 9 | 90 |

In Table 8, Group A rabbits (n=5) were not given any endotoxin at time zero, and were given saline injections free of IL-1ra at the periodic injection times. Group B rabbits (n=10) were given 0.5 mg/kg of body weight of endotoxin at time zero, and the periodic injections were again free of IL-1ra. After 7 days the survival rate of rabbits in Group B was only 20%.

In Groups C–E (n=10), endotoxin was administered at time zero, and the saline injections contained varying amounts of IL-1ra. The rabbits in Group C received a total of 10 mg/kg of body weight of IL-1ra. The rabbits in Group D received a total of 30 mg/kg of body weight of IL-1ra. And finally, the rabbits in Group E received a total of 100 mg/kg of body weight of IL-1ra. After 7 days, the survival rate of rabbits in Group E was 90%.

This experiment shows that treatment with IL-1ra significantly delays and reduces final mortality rates in rabbits with endotoxin induced shock.

EXAMPLE 8

Effects of Human IL-1ra on Ischemia and Reperfusion Injury

In the following example experimental dogs were subjected to regional myocardial ischemia for two hours and then reperfused for 4 hours. The dogs were divided into two groups, one group treated with IL-1ra and the other treated with serum albumin in the same buffer used for the test group.

Animals were fasted overnight and on the following morning, were anesthetized with 10 ml of thiamylal sodium 5%, followed by 2 ml of sodium pentobarbital 6%, intravenously. Additional sodium pentobarbital was administered during the experiment as necessary. Artificial respirator. A left thoracotomy was performed through the fifth intercostal space and polyvinyl catheters placed in the left internal jugular vein for fluid and drug administration, and in the left internal carotid artery and femoral arteries for pressure monitoring and withdrawal of reference blood samples. A catheter was placed in the left atrium for injection of radio active microspheres. The left circumflex artery was dissected free of surrounding tissue and an electromagnetic flow probe was placed on the vessel proximal to the first obtuse marginal branch. After an intravenous bolus injection of 50 mg of lidocaine, the circumflex coronary artery was occluded with the snare occluder for 2 hours. Complete occlusion was verified with the electromagnetic flow probe. The snare was then released suddenly, allowing reperfusion of the coronary vascular bed for 4 hours.

Two-dimensional echocardiograms and hemodynamic measurements (heart rate, blood pressure and left atrial pressure) was determined before occlusion, after 110 minutes of occlusion, 5 minutes after reperfusion, and 4 hours after reperfusion. Two-dimensional echocardiography was performed with the use of a scanner and a 2.25 MHz transducer. The transducer was placed on the closed shaved right chest and was allowed full visualization of the circumferential extent of the left ventricle in a short-axis projection. Echocardiographic images were recorded at the midpapillary muscle position onto a video cassette with use of a Sony recorder. A two dimensional echocardiographic analysis was performed with the use of a minicomputer-based video digitizing system.

End-diastolic and end-systolic frames were selected for analysis with the use of the onset of the Q wave in lead II as a marker of end-diastole and the smallest left ventricular cavity size as a marker of end-systole. Endocardial and epicardial borders for 3 consecutive beats during normal sinus rhythm was carefully traced directly from the video display onto a digitizing tablet. Quantitative analysis was performed with a radial contraction model and a fixed diastolic center of mass at 22.5 degree intervals over the full left ventricular circumference.

The midpoint of the posterior papillary muscle was chosen as a fixed anatomic reference and designated as 135 degrees. Wall thickening was computed for each of the 22.5 degree sectors with the following equation: wall thickening=[(end systolic wall thickness−end diastolic wall thickness)/end diastolic wall thickness]×100%. The normal range of wall thickening was determined from a functional map of the baseline images for three cardiac cycles and 95% tolerance limits were established in each animal. These limits were used for comparison with occlusion and reperfusion functional maps and abnormalities are expressed as the circumferential extent of dysfunction and the degree of dysfunction. The extent of dysfunction (in degrees) was measured at the intercepts between the occlusion or reperfusion maps and the lower 95% tolerance limit; the degree of dysfunction (in area units) is the planimetered area below the lower 95% tolerance limit.

Regional myocardial blood flow was assessed by the reference withdrawal method using tracer-tabled microspheres (15 μm diameter, New England Nuclear) injected into the left atrium. The microspheres were ultrasonicated and vortex-agitated before injection. Microspheres were injected before occlusion, after 110 minutes of occlusion, 5 minutes after reperfusion and 4 hours after reperfusion with one of six available isotopes ($^{141}$Ce, $^{51}$Cr, $^{113}$Sn, $^{103}$Ru, $^{95}$Nb, $^{46}$Sc). Simultaneous reference arterial samples were withdrawn from the carotid and femoral arteries at a constant rate of 7 ml/minute with a Harvard withdrawal pump starting 10 seconds before microsphere injection and continuing for 120 seconds after completion of the injection.

Two adjacent transverse left ventricular slices at the midpapillary muscle level, corresponding to the echocardiographic short-axis slices, were selected for blood flow determination. Each slice was divided into 16 full-thickness 22.5 degree sectors. Each sector was then further divided into epicardial, midmyocardial, and endocardial samples. The tissue samples were then weighed, placed in counting vials, and assayed for radioactivity in a gamma scintillation counter. After background and overlap correction, absolute myocardial blood flow was calculated with the following equation: Qm=(Cm×Qr/Cr), where Qm=myocardial blood flow (ml/min); Cm=counts/min in tissue sample; Qr=withdrawal rate of the reference arterial sample (ml/min); Cr=counts/min in the reference arterial sample. Myocardial blood flow is expressed per gram of tissue for each sample.

Just prior to sacrifice, the left circumflex coronary artery was briefly occluded and monastral blue pigment (0.5 ml/kg) injected into the left atrium for delineation of the in vivo myocardial area at risk. The animal then received 3000 U of heparin and was sacrificed with an intravenous bolus of saturated KCl solution and the heart excised.

Treatment Groups. Dogs were randomly assigned to one of two groups. In the test group, dogs received a bolus injection of 30 mg IL-1ra just prior to the onset of the ischemia and 15 mg IL-1ra for each hour until the experiment was terminated. Control animals received an identical quantity of endotoxin-free, human albumin dissolved in the same buffer used for the test group.

Determination of Infarct Size. After death, the heart of each dog was excised, the left ventricle isolated from surrounding tissue, cooled in a freezer for 15 minutes, and then sliced into 5 mm transverse sections. The slices were then weighed and placed in a warm bath of buffered triphenyl tetrazolium chloride for ten minutes. In this technique, viable tissue stains red while nonviable tissue remains unstained (*Am. Heart J.,* 101:593). The unstained zone of infarcted tissue is outlined on transparent overlays and quantitated by planimetry using a microcomputer and corrected for the weight of the heart slice. Infarct size is expressed as the percentage of the area of mycoardium at risk (the area at risk of infarction is defined as the area of the myocardium left unstained following the injection of monastral blue into the left atrium).

NMR Analysis of Myocardial Edema. After fixation, the hearts were cut into 5 to 7 transverse slices approximately 5 mm thick. Two transmural myocardial tissue samples were obtained from the nonischemic zone (positive monastral blue staining) and the central ischemic zone (negative blue staining). The epicardium for each sample was dissected away to eliminate possible lipid signal interference. Each piece was subdivided transmurally (weighing approximately 500 mg each) with one portion assessed for % $H_2O$ by dessication technique (wet weight–dry weight/wet weight) while the other was placed into a clean dry glass tube. T1 and T1 relaxation times were obtained on a IBM PC 20 Minispec spectrometer (IBM Instruments, Inc., Danbury, Conn.) operating at 20 MHz and 40° C. The location of the sample in the magnet, 90° and 180° radio frequency pulses, and detector phase were optimized for each sample before relaxation measurements were obtained. T1 values were determined by a fit of 20 inversion data recovery points while T2 values were determined by using a Carr, Purcell, Meiboon-Gill (CPMG) sequence. In an attempt to minimize effects of diffusion and miscellaneous system instabilities, the 180° radio frequency interpulse spacing was maintained at 180 microseconds. The fraction of echo samples determined were used as variables to adjust the duration of the CPMG experiment. Typically, 1 to 150 data points were acquired as the echo train was delayed to 15% to 25% of its original amplitude. T2 values were determined by using a multi-exponential fit. Only the dominant component of the exponential fit was used for statistical analysis. The results of the T1 and T2 analysis were corrected with percent water for adjacent tissue samples to verify the accuracy of the NMR technique.

Histologic and Morphometric Evaluations. For each group tested at least 3 animals were evaluated by light microscopy. Sections stained with hematoxylin and eosin from each heart were evaluated for neutrophil accumulation within the area between viable and infarcted tissue.

Statistical Analysis. All data was represented as the mean±S.E.M. Comparisons within groups were made by a two-way analysis of variance. When significant F values are obtained, paired t tests (corrected for multiple comparisons with the Bonferroni inequality adjustment) will be used to determine which measurements differed significantly from one another.

Comparisons between groups were made by unpaired t test. An exponential regression was used to correlate infarct size data to myocardial blood flow.

The results of the IL-1ra treatment regimen on protecting dog myocardium from occlusion reperfusion injury, are listed in Table 9 below. As a percentage of the left ventricular mass, the influx infarct size in the treated group was reduced to 10.3% as opposed to 18.2% in the control animals. This result represents a 40% reduction in the percent of the left ventricular mass that was infarcted. The percentage of the area at risk, in contrast, was not markedly changed, 40.5% of the left ventricular mass in the treated group versus 44.8% in the control animals. When the infarcted area is calculated as a percent of the total area at risk, the numbers similarly favor the IL-1ra treated animals, 24.9% versus 42% in the control group.

TABLE 9

THE EFFECT OF IL-1ra IN REDUCING THE EXTENT AT INFARCTED TISSUE IN CANINE CORONARY OCCLUSION-REPERFUSION STUDIES

|  | IL-1ra Treated (n = 9) | Albumin Treated (n = 9) |
| --- | --- | --- |
| Infarct size as a % of left ventricular mass | 10.3% ± 2.2% | 18.2% ± 3.3% |
| Area at risk as a % of left ventricular mass | 40.5% ± 1.7% | 44.8% ± 1.9% |
| Infarct size as a % of mass at risk | 24.9% ± 4.6% | 42% ± 8.3% |

EXAMPLE 9

In Vivo Effects of IL-1ra on MBP-Induced EAE

Female Lewis rats (150–200 g) were purchased from Charles River Raleigh, N.C.), and housed at Synergen for at least 1 week before starting experiments. They received food and water ad libitum and housed in temperature and light controlled (12 h/day) rooms. Within each experiment, animals were age-matched.

EAE induction and evaluation. Rats (usually six/group) were anesthetized with 2% isoflurane+$O_2$ and immunized on day 0 in the footpad of the left hind limb with 0.1 ml of an emulsion containing MBP at one of the following doses 0, 3, or 30 µg (fragment 68–84 Bachem Bioscience, PA) dissolved in phosphate buffered saline (PBS) with an equal volume of complete Freund's adjuvant (CFA) containing 5 mg/ml of *Mycobacterium tuberculosis* H37Ra (Difco Lab MI). Control rats received 0.1 ml of the PBS/CFA emulsion with no MBP in the footpad of the left hind limb.

Evaluation of clinical disease was based on a conventional 0–5 scoring system. Briefly, the spectrum of rating was 0 normal, 0.5 partial loss of tail tone, 1 complete loss of tail tone, 2 dragging of one hind limb, 3 paralysis of both hind limbs, 4 morbid, and 5 death. Clinical severity was assessed on a daily basis. Daily weights were recorded for individual rats and weight loss/gain was expressed relative to initial weight.

The inhibitory effects of IL-1ra on clinical severity expressed as area under curve (Units arbitrary) were determined for each group and compared statistically against the vehicle group using the Mann-Whitney test. In addition to the clinical severity indices, mean weight gain for each group was determined and compared statistically (students t-test). In all of these studies no significant differences at any of the MBP doses were observed between the no vehicle and vehicle dosed groups.

The 3 and 30 µg MBP doses were used in the IL-1ra related studies, because the 3 µg and 30 µg doses were approximately submaximal and maximal for clinical symptoms without causing death in this model. All injections of IL-1ra (100 mg/kg) or diluent (CSE buffer: 10 mM citrate, 140 mM NaCl, 0.5 mM EDTA) control were given subcutaneously. IL-1ra or vehicle was administered every 6 hrs for 12 days beginning on day nine post MBP. In each experiment, the control rats received the same number of injections as the treatment groups to diminish any secondary effects due to stress.

Initial studies assessed the clinical severity of different doses of MBP (0.1–30 µg/0.1 ml) in the rat. The 0.1 and 0.3 µg MBP doses produced no apparent clinical symptoms. The 30 µg dose of MBP produced the most serve clinical symptoms, compared to the 1 µg dose. This effect was highly significant (p<0.001, Mann-Whitney U-test). Onset of clinical symptoms varied from individual animal and on the concentration of MBP used, but significant differences between MBP doses were observed. In general, increasing the dose (1–30 µg) of MBP produced clinical symptoms earlier, for example 1 µg MBP had a mean±S.E.M. onset of 14.88±0.42 (n=9) compared to 12.35±0.16 (n=34; p<0.01) days for the 30 µg MBP dose. In addition, a dose dependent effect of MBP (1–30 µg) on weight loss was observed. Animals spontaneously recovered from the clinical symptoms within 5–7 days of onset. Administration of CFA alone produced no clinical symptoms, however, there was an initial transient weight loss compared to non-treated controls.

Effect of IL-1ra. To determine if inhibiting endogenous IL-1 in vivo would affect the development of EAE, daily (4× a day subcutaneously) injections of 100 mg/kg IL-1ra were initiated 9 days post MBP immunization and continued until day 21. IL-1ra significantly inhibited clinical symptoms induced by 3 (p<0.032) and 30 µg MBP (p<0.001) compared to vehicle controls. The IL-1ra treated groups exhibited a delay in the mean onset of clinical symptoms. For example, animals that received vehicle had a mean onset time of 13.8 and 11.5 days for the 3 or 30 µg MBP respectively, compared to the IL-1ra treated animals of 15.25 and 13.4 days, respectively.

Figure 5:
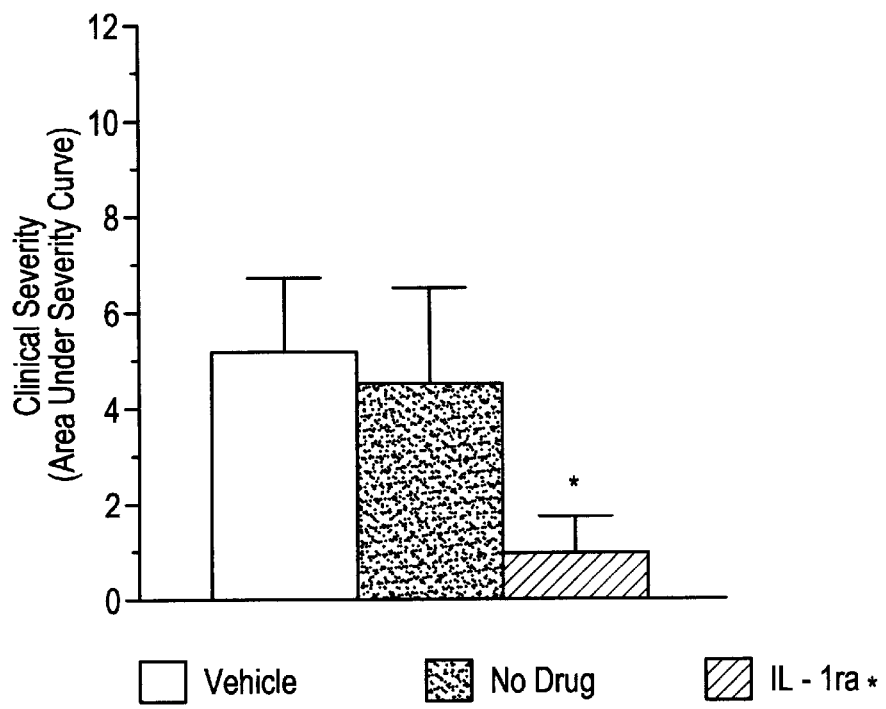
FIG. 5 shows the in vivo effects of IL-1ra (100 mg/kg) on an animal model with EAE induced with 3 μg of MBP ($p<0.032$).
Figure 6:
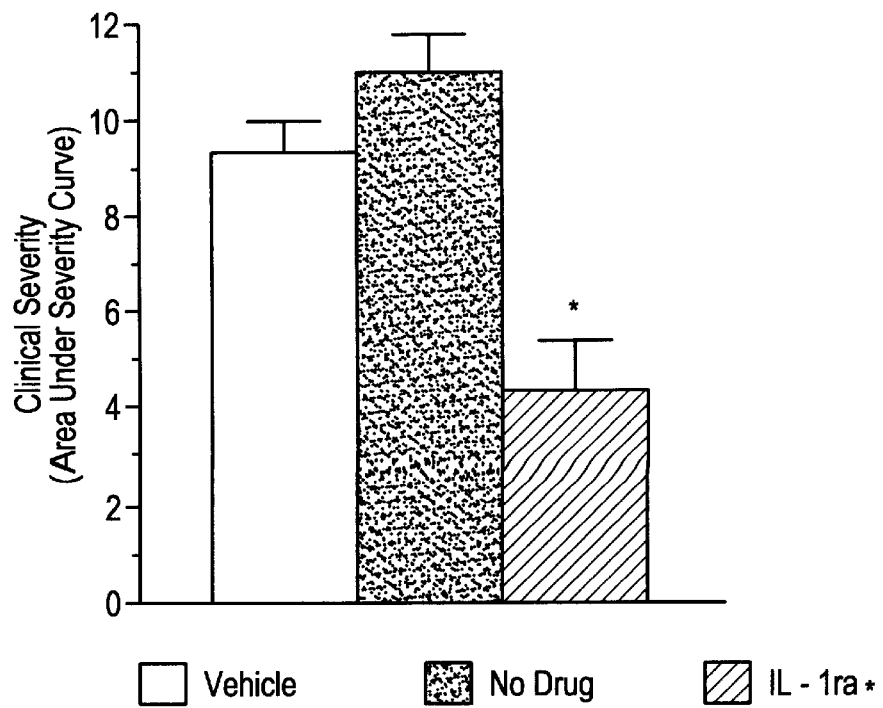
FIG. 6 shows the in vivo effects of IL-1ra (100 mg/kg) on an animal model with EAE induced with 30 μg of MBP (p<0.01).

At both doses of the MBP (3 µg or 30 µg) IL-1ra (100 mg/kg) decreased the duration of the clinical symptoms by 55% and 29% respectively compared to the vehicle groups (FIGS. 5 and 6).

Figure 7:
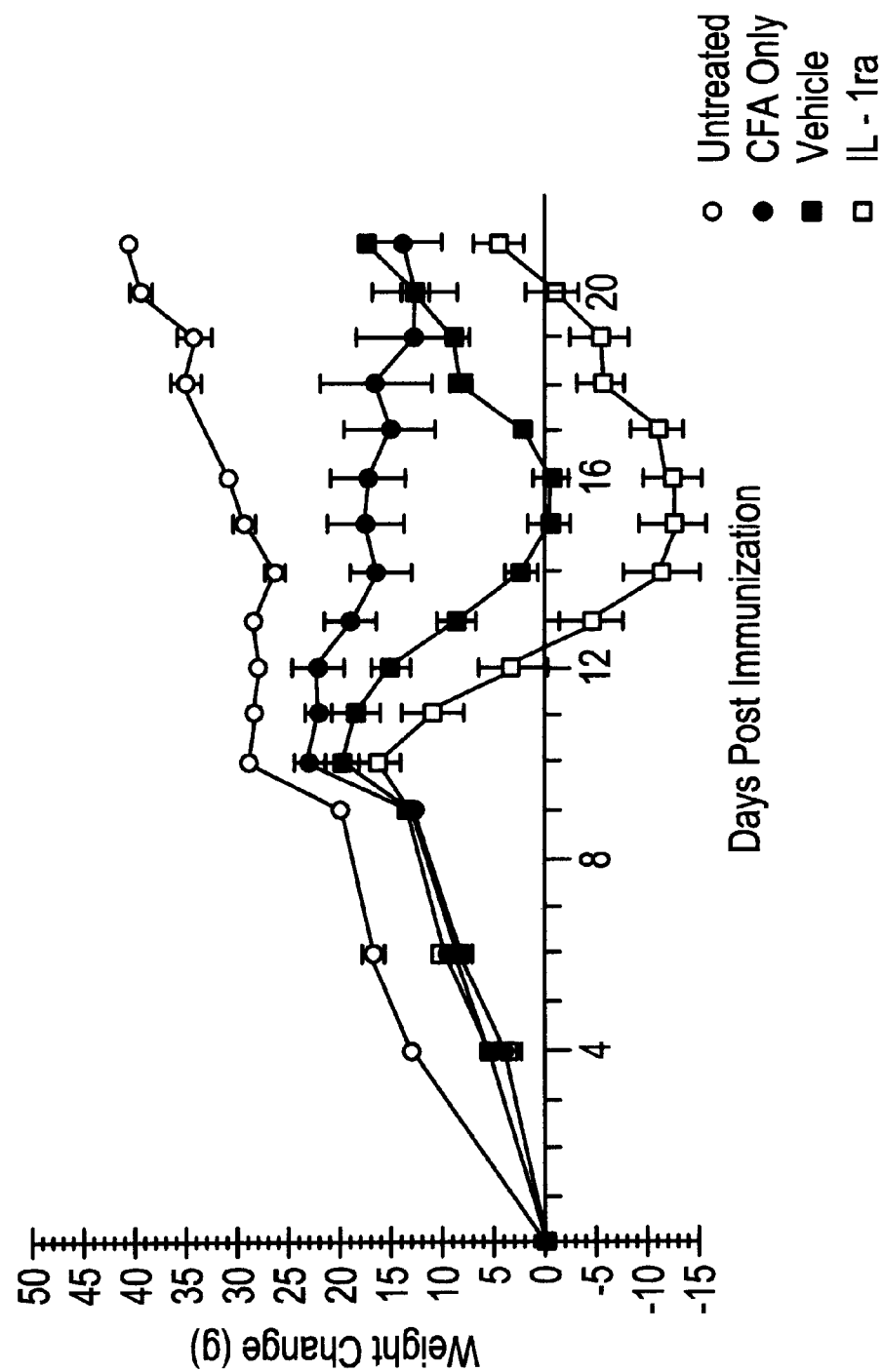
FIG. 7 shows the weight change from day 0 in rats immunized with 30 μg MBP and treated with 100 mg/kg IL-1ra.

Weight loss is an important marker of EAE onset, and rats that received IL-1ra (100 mg/kg) lost less weight compared to the vehicle groups (FIG. 7). The average weight gain for the 3 and 30 µg MBP groups that received vehicle over the 21 day study were 10±1.71 g and 4.6±2.2 g. The IL-1ra groups using similar doses of MBP (3 and 30 µg) had a significant weight gain compared to the vehicle groups 19±2.5 g and 17.6±0.42 g (p<0.05, p<0.01 unpaired t-test). The normal weight gain in unmanipulated animals over the same time period was 40±0.516 g.

The results implicate the involvement of endogenous IL-1 in EAE induction because treatment with the receptor antagonist (IL-1ra) reduced clinical disease. This most likely occurred by IL-1ra specifically binding to the IL-1 receptor complex thus preventing the binding of the natural endogenous ligand IL-1.

IL-1ra not only decreased the severity of the disease but there was also a trend in reducing EAE duration. Furthermore, the onset of the disease was also delayed by IL-1ra. Inhibition of weight loss due to IL-1ra treatment may have been secondary to suppression of EAE or due to blocking the ability of IL-1 to stimulate or synergize with TNF (Flores et al., 1989). It is also possible since IL-1ra reduced clinical symptoms, that animals found it easier to obtain food and water compared to their vehicle controls.

The IL-1ra treatment may have limited perivascular infiltration of cells into the CNS by preventing an IL-1-induced increase in adhesion molecule expression on the CNS vasculature. Astrocyte hyperplasia and gliosis result in the formation of CNS plaques associated with MS. As IL-1 has been shown to induce astrocyte proliferation, IL-1ra treatment may have prevented IL-1 induction of astrocyte hyperplasia. Finally, by interfering with the activity of IL-1, IL-1ra may have blocked the induction of other cytokines within the CNS that are involved in mediating the clinical and pathological sequela of EAE.

These studies have shown that selective inhibition of IL-1 by administering IL-1ra in vivo can reduce the clinical severity, duration and delay disease onset of the inflammatory CNS disease (EAE). Thus the IL-1 antagonist is therapeutically beneficial for certain inflammatory CNS diseases such as MS.

EXAMPLE 10

Effects of IL-1ra in Cerebral Ischemia

The objective of the experiments reported in this Example was to investigate the involvement of endogenous IL-1 in the damage following hypoxia-ischemia. To examine this hypothesis in neonatal brain IL-1ra was tested using an in vivo experimental rat model of hypoxic-ischemic forebrain injury. The neonatal brain hypoxic-ischemic model is widely recognized as a reliable and clinically relevant experimental procedure as a animal model of brain damage that can occur in cerebral palsy. Weighing the hemispheres has been shown to be a reliable method in quantifying tissue loss (Andine et al., *J. Neurosci. Meth.*, 35:253–260 (1990).

In the experiments, 7-day-old rats were used that had undergone a unilateral carotid ligation and subsequent exposure to 2 hours of 7.5% oxygen. This is a well characterized small animal model for perinatal hypoxic-ischemic encephalopathy (Rice et al., *Ann. Neurol.*, 9:131–141 (1981). This model, a variation of the preparation described in Levine, *Am. J. Pathol.*, 36:1–17 (1960) produces a unilateral brain injury, as described by Rice and colleagues. Neither unilateral carotid ligation nor hypoxia alone causes microscopically visible changes. Together, the two manipulations produce a spectrum of injury, varying according to the duration of hypoxia. The age of the rats were chosen because the development of rat brain at this stage resembles the maturational level of the full term human neonate. The pathogenesis of neuronal injury appears to be related to pressive ischemia that develops as the duration of hypoxic exposure lengths. The combination of moderate hypoxemia and ischemia causes a reproducible pattern of acute and chronic ischemic neuronal changes in the forebrain ipsilateral to carotid occlusion. Foci of infarction in the corpus striatum, hippocampus and cortex occur commonly, surrounded by areas of disrupted neuronal organization. The infarctions resemble the pattern of injury now being recognized more frequently in human infants as reported in Hill et al., *Pediatrics*, 71:790–93 (1983).

In the experiments, seven day old male and female (Sprague-Dawley) rats were anesthetized with 2% isoflurane+$O_2$ and body temperature was maintained within normal limits. The neck region was prepped with betadine solution before surgery. A small incision was made so that the left carotid artery was exposed. The carotid artery was electrocauterized between double ligatures of silk suture. The wound was closed with suture and the rats were placed back into a cage containing their dam to recover before they were placed into a chamber that contained either 20% or 7.5% $O_2$ in nitrogen.

After the rats had recovered from the anesthesia, they were placed into a chamber for 2 hours that was constantly gassed with either 7.5% (hypoxic environment) or 20% (normoxic environment) $O_2$ balanced nitrogen gas mixtures. The chamber was kept at 36° C. by placing it in a heated water bath. After this procedure the rats were returned to their dams.

IL-1ra (100 mg/kg subcutaneously) or vehicle (ml/kg subcutaneously) was administered either 1 hr prior to the hypoxic chamber, or at time O, 1 or 3 hr post hypoxic insult and then at the following times 5, 9, 20 & 28 hrs.

Rats were sacrificed two weeks later and ipsilateral and contralateral brain hemisphere weights determined (wet weight) and then placed into a oven at 70° C. for 36 hrs (dry weight). Right and left hemisphere weight disparities were compared as percent reductions ([(L−R)/R]×100). During this phase of rapid brain growth, reduction in hemisphere weight can be used as an indicator of injury more readily than in adults. Hemispheric brain weight disparity, validated in this model as a quantitative measure of brain injury according to Andine et al., *J. Neurosci. Meth.*, 35:253–260 (1990), incorporated herein by reference, was determined.

In vehicle treated animals, the ischemic/hypoxic insult produced marked infarcts, the ipsilateral hemisphere being visually smaller in size and necrotic. In the vehicle treated animals the difference between the ipsilateral (0.5087±0.019 gms) and the contralateral (0.62±0.014 gms, n=19) hemispheres was approximately 120 mg, whereas the IL-1ra treated rats this difference was smaller 35 mg.

IL-1ra (100 mg/kg s.c.) administered prior or after the ischemic/hypoxic insult ameliorated the ischemic damage as measured by hemisphere weights. There was a reduction in the difference between the ipsilateral and contralateral hemisphere weights suggesting that IL-1ra was neuroprotective. IL-1ra was effective whether it was administrated 1 hour before or 1 hour after the ischemic/hypoxic insult.

When compared to vehicle treated hypoxic-ischemic controls, IL-1ra administered 1 hour prior to the ischemic-hypoxic insult and then after the ischemic-hypoxic insult at the time points indicated (1, 3, 5, 9, 20 and 28 hrs) was very effective in reducing cerebral hemisphere damage. Cerebral hemisphere weights in rats that underwent unilateral hypoxic-ischemic forebrain injury treated with either vehicle or IL-1ra 1 hr prior to the insult were determined as follows: vehicle treated: −20.84±4.2 (n=10); IL-1ra treated: −9.14±3.5 (n=10) ($p<0.05$). Littermate pups were treated with vehicle or IL-1ra immediately after the hypoxic-ischemic insult. The initial administration of IL-1ra at 0 hr after the insult was still effective in reducing cerebral hemisphere damage as shown by the following results: vehicle treated: −11.71±2.31 (n=16); IL-1ra treated: −0.168±2.50 (n=18) ($p<0.01$). Delaying the first administration of IL-1ra further to 1 hr post ischemic-hypoxic insult resulted in significant ($p<0.01$) reduction of cerebral hemisphere damage as shown by the following results: vehicle treated: −20.29±3.93 (n=20); IL-1ra treated: −5.16±2.0 (n=19). Further delays of the first dose of IL-1ra (3 hrs post insult) reduced the cerebral hemisphere damage as shown by the following results: vehicle treated: −12.78±3.74 (n=11); Il-1ra treated: −5.54±4.5 (n=11), but the reduction was not significantly different from vehicle treated animals.

Animals that did not undergo surgery and were placed in a normoxic (20% oxygen) environment, received IL-1ra or vehicle at the same dosing frequency as indicated above. These animals had normal hemisphere weights indicating that IL-1ra had no obvious effects on developing normal brain tissue.

In the present study, IL-1ra had little or no effect on normal brain tissue. In contrast, peripheral administration of IL-1ra reduced the damaged associated with the hypoxic-ischemic episode. It was possible in this model to delay the administration for up to 1 hr post insult and still retain significant neuroprotection. Further delay in the administration of IL-1ra was less effective, but there was still evidence of a neuroprotective role as indicated by the weight differences between the ischemic and non-ischemic hemispheres compared to vehicle treated animals. These data indicate that endogenous IL-1 is an important mediator of neuronal damage in this model since the IL-1 antagonist IL-1ra reduced the tissue damage.

The foregoing description of the invention is exemplary for purposes of illustration and explanation. It will be apparent to those skilled in the art that changes and modifications are possible without departing from the spirit and scope of the invention. It is intended that the following claims be interpreted to embrace all such changes and modifications.

What is claimed is:

1. A method for treating reperfusion injury comprising administering to a patient in need thereof a therapeutically effective amount of an interleukin-1 receptor antagonist (IL-1ra), wherein said IL-1ra comprises a polypeptide that inhibits IL-1 and is sufficiently pure such that at least a portion of the amino acid sequence of said polypeptide can be determined, wherein said polypeptide comprises (1) the following amino acid sequence:
    (U) Arg Pro Ser Gly Arg Lys Ser Ser Lys Met Gln Ala Phe Arg Ile Trp Asp Val Asn Gln Lys Thr Phe Tyr Leu Arg Asn Asn Gln Leu Val Ala Gly Tyr Leu Gln Gly Pro Asn Val Asn Leu Glu Glu Lys Ile Asp Val Val Pro Ile Glu Pro His Ala Leu Phe Leu Gly Ile His Gly Gly Lys Met Cys Leu Ser Cys Val Lys Ser Gly Asp Glu Thr Arg Leu Gln Leu Glu Ala Val Asn Ile Thr Asp Leu Ser Glu Asn Arg Lys Gln Asp Lys Arg Phe Ala Phe Ile Arg Ser Asp Ser Gly Pro Thr Thr Ser Phe Glu Ser Ala Ala Cys Pro Gly Trp Phe Leu Cys Thr Ala Met Glu Ala Asp Gln Pro Val Ser Leu Thr Asn Met Pro Asp Glu Gly Val Met Val Thr Lys Phe Tyr Phe Gln Glu Asp Glu
    wherein (U) is nothing or Met; or
    (2) a sequence which is at least about 90% homologous to said amino acid sequence.

2. The method of claim 1, wherein said IL-1ra is glycosylated.

3. The method of claim 1, wherein said IL-1ra is non-glycosylated.

4. The method of claim 3, wherein said IL-1ra is methionyl IL-1ra.

5. The method of claim 1, wherein said IL-1ra is produced by recombinant DNA methods.

6. A method according to claim 1, wherein said polypeptide comprises the following amino acid sequence:
(U) Arg Pro Ser Gly Arg Lys Ser Ser Lys Met Gln Ala Phe Arg Ile Trp Asp Val Asn Gln Lys Thr Phe Tyr Leu Arg Asn Asn Gln Leu Val Ala Gly Tyr Leu Gln Gly Pro Asn Val Asn Leu Glu Glu Lys Ile Asp Val Val Pro Ile Glu Pro His Ala Leu Phe Leu Gly Ile His Gly Gly Lys Met Cys Leu Ser Cys Val Lys Ser Gly Asp Glu Thr Arg Leu Gln Leu Glu Ala Val Asn Ile Thr Asp Leu Ser Glu Asn Arg Lys Gln Asp Lys Arg Phe Ala Phe Ile Arg Ser Asp Ser Gly Pro Thr Thr Ser Phe Glu Ser Ala Ala Cys Pro Gly Trp Phe Leu Cys Thr Ala Met Glu Ala Asp Gln Pro Val Ser Leu Thr Asn Met Pro Asp Glu Gly Val Met Val Thr Lys Phe Tyr Phe Gln Glu Asp Glu
wherein (U) is nothing or Met.

7. The method according to claim 6, wherein the polypeptide is substantially pure.

8. The method according to claim 1, wherein the IL-1ra is IL-1rax, IL-1raα or IL-1raβ.

9. The method according to claim 1, wherein said polypeptide is linked to a polymeric material.

10. The method of claim 9, wherein the polymeric material is polyethylene glycol.

11. The method of claim 1, 9, or 10, wherein the polypeptide is administered in a pharmaceutical composition.

12. The method according to claim 6, wherein said polypeptide is linked to a polymeric material.

13. The method of claim 12, wherein the polymeric material is polyethylene glycol.

14. The method of claim 6, 12 or 13, wherein the polypeptide is administered in a pharmaceutical composition.

15. The method of claim 11, wherein said pharmaceutical composition comprises the polypeptide and a carrier, wherein said composition is a pharmacologically-compatible, slow-release formulation.

16. The method of claim 14, wherein said pharmaceutical composition comprises the polypeptide and a carrier, wherein said composition is a pharmacologically-compatible, slow-release formulation.

17. The method of claim 6, wherein said polypeptide consists of the following (U) Arg Pro Ser Gly Arg Lys Ser Ser Lys Met Gln Ala Phe Arg Ile Trp Asp Val Asn Gln Lys Thr Phe Tyr Leu Arg Asn Asn Gln Leu Val Ala Gly Tyr Leu Gln Gly Pro Asn Val Asn Leu Glu Glu Lys Ile Asp Val Val Pro Ile Glu Pro His Ala Leu Phe Leu Gly Ile His Gly Gly Lys Met Cys Leu Ser Cys Val Lys Ser Gly Asp Glu Thr Arg Leu Gln Leu Glu Ala Val Asn Ile Thr Asp Leu Ser Glu Asn Arg Lys Gln Asp Lys Arg Phe Ala Phe Ile Arg Ser Asp Ser Gly Pro Thr Thr Ser Phe Glu Ser Ala Ala Cys Pro Gly Trp Phe Leu Cys Thr Ala Met Glu Ala Asp Gln Pro Val Ser Leu Thr Asn Met Pro Asp Glu Gly Val Met Val Thr Lys Phe Tyr Phe Gln Glu Asp Glu wherein (U) is nothing or Met.

18. The method of claim 17, wherein the polypeptide is administered in a pharmaceutical composition.

19. The method of claim 18, wherein the pharmaceutical composition comprises the polypeptide and a carrier, wherein the composition is a pharmacologically-compatible, slow-release formulation.

\* \* \* \* \*

UNITED STATES PATENT AND TRADEMARK OFFICE
CERTIFICATE OF CORRECTION

| | |
|---|---|
| PATENT NO. | : 6,159,460 |
| DATED | : December 12, 2000 |
| INVENTOR(S) | : Thompson et al. |

It is certified that error appears in the above-identified patent and that said Letters Patent is hereby corrected as shown below:

<u>Title page,</u>
Item [63], line 11, insert after "abandoned" the following:
-- which is a continuation of application No. 07/248,521, September 23, 1988, abandoned, which is a continuation-in-part of application No. 07/238,713, August 31, 1988, abandoned, which is a continuation-in-part of application No. 07/199,915, May 27, 1988, abandoned --

<u>Column 11,</u>
Line 13, delete "is".
Line 45, change "Saklatvala" to -- Saklatavala --.
Line 63, change "Theumatol." to -- Rheumatol. --.

<u>Column 20,</u>
Table 7, line 4, change "0.8" to -- 0/8 --.

<u>Column 29,</u>
Line 19, insert after "following", -- amino acid sequence: --.

Signed and Sealed this

Eighteenth Day of November, 2003

JAMES E. ROGAN
*Director of the United States Patent and Trademark Office*